(12) United States Patent
Averianov et al.

(10) Patent No.: US 7,041,074 B1
(45) Date of Patent: May 9, 2006

(54) DEVICE FOR USERS SUFFERING FROM SEQUELS OF CENTRAL NERVOUS SYSTEM AND LOCOMOTRIUM AFFECTION OF BODY

(76) Inventors: Andrei Igorevich Averianov, Ul. Timiryazevskaya, d. 32, korp.2, kv. 48, Moscow 125422 (RU); Ksenia Alexandrovna Semenova, ul. Druzhby, d. 2/19, kv. 54, Moscow, 117330 (RU); Vitaly Vitorovich Chugunov, ul. Butyrskaya, d. 3, kv. 80, Moscow, 12505 (RU)

( * ) Notice: Subject to any disclaimer, the term of this patent is extended or adjusted under 35 U.S.C. 154(b) by 494 days.

(21) Appl. No.: 09/885,414

(22) Filed: Jun. 21, 2001

(30) Foreign Application Priority Data

Jun. 21, 2000 (RU) .......................................... 2000115794

(51) Int. Cl.
*A61F 5/00* (2006.01)

(52) U.S. Cl. .............................. 602/20; 602/19; 602/23; 128/845; 128/846

(58) Field of Classification Search ................... 602/20, 602/12, 16, 19, 21, 22, 23, 60, 24–30; 128/95.1, 128/96.1, 98.1, 99.1, 845, 846, 869; 601/33, 601/34, 35; 403/52; 482/51, 66
See application file for complete search history.

(56) References Cited

U.S. PATENT DOCUMENTS

| | | | | |
|---|---|---|---|---|
| 4,543,948 A | * | 10/1985 | Phillips et al. ................. | 602/23 |
| 4,602,627 A | * | 7/1986 | Vito et al. ...................... | 602/23 |
| 5,188,584 A | * | 2/1993 | Petrofsky et al. .............. | 602/16 |
| 5,407,420 A | * | 4/1995 | Bastyr et al. .................. | 602/20 |
| 5,476,441 A | * | 12/1995 | Durfee et al. .................. | 602/23 |
| 5,658,242 A | | 8/1997 | McKay et al. | |
| 5,749,840 A | * | 5/1998 | Mitchell et al. ............... | 602/26 |
| 5,961,476 A | * | 10/1999 | Betto et al. .................... | 602/16 |
| 6,024,713 A | * | 2/2000 | Barney ......................... | 602/23 |
| 6,361,513 B1 | * | 3/2002 | Rossi et al. .................... | 602/16 |
| 6,764,457 B1 | * | 7/2004 | Hogg ............................ | 602/23 |

FOREIGN PATENT DOCUMENTS

RU 2131232 6/1999

OTHER PUBLICATIONS

Catalogue of Orthopedic Devices, Ognoniole, M., Orthopedii, Russia.

* cited by examiner

*Primary Examiner*—Fadi H. Dahbour
(74) *Attorney, Agent, or Firm*—I. Zborovsky

(57) ABSTRACT

A device for users with sequels of central nervous system affections and/or locommotorium affection of a body has a plurality of modules covering areas of the user's body, a recliner with bands for embracing shoulder joints, a structure for correcting a medium area of the user's body, a structure for correcting lower extremities of the user's body, a structure for correcting feet of the user's body, as well as correction rotating elements and connecting elements.

18 Claims, 5 Drawing Sheets

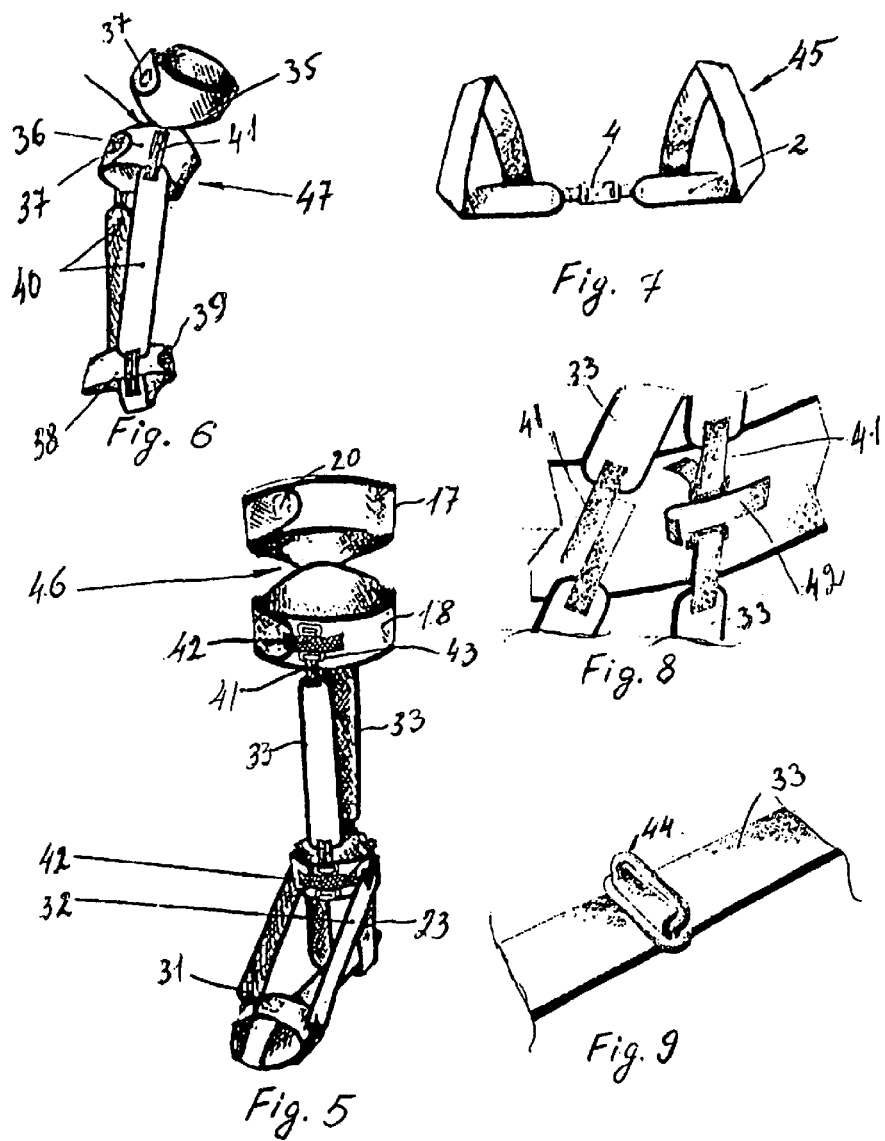

DEVICE FOR USERS SUFFERING FROM SEQUELS OF CENTRAL NERVOUS SYSTEM AND LOCOMOTRIUM AFFECTION OF BODY

FIELD OF APPLICATION

The present invention relates to medicine, and more particularly to a device for treating of patients with sequels of central nervous system and/or locomotorium affection of body.

The present invention can be used in neurology, neurosurgery, tramatology, orthopedics and cardiology, in particular for treatment of patients with child cerebral paralysis, patients with injuries of spine, possibly with complications by injuries to bone marrow, patients with osteo khondro dystrophy, scoliosis, kifo scoliosis, patients with complications of skull-brain traums and acute disturbances of brain blood circulation, and also for rehabilitation in condition of diseases of cardiovascular system.

In addition, the proposed device can be used for correction of stateliness of the user, and also as exercises of different types for performing sports exercises.

Presumptions for Creation of the Invention

The problems of treating of above mentioned diseases is very important due to the presence of a great number of patients which suffer from such diseases. In the whole world there is a tendency toward growth of the number of patients with these diseases. The importance of treating of the above mentioned diseases is determined not only by the presence of a great number of patients, but also by a quality of the known methods of treatment.

In the present time various devices are known for restoration of local motorium functions of various parts of bone-muscle system of a person.

For example, practically all known orthopedic devices for treatment of pathologies of lower limbs (both metal-plastic and splint-laser) represent a so-called "exterior skeleton" which protects the functions of muscles and capsule-connection apparatus of joints of the limbs. The U.S. Pat. No. 5,658,242 describes a device for facilitating of local motorium functions of lower limbs which includes a waste supporting element (bandage) which is connected through a resilient-elastic connection with shin-foot supporting bandages and supporting bandages for a hip. The above mentioned bandages are connected with one another by rigid braces, which in their medium part at the level of a knee joint has a hinge connection.

This device provides a removal of stress from the muscles of a leg during walking and contributes to some restoration of local motorium functions of the legs of the user, which had a trauma and disease of lower limbs.

However, the use the rigid (exterior skeleton) leads to a weakening a hypertrophy of the muscles of the lower limbs.

During treatment of bone-muscle system of upper limbs known devices for treatment of various parts of the upper limbs can be used, for example "Unloading bandage on an upper limb (left/right)", "Bandage of" "Bandage on a wrist", "Splint of a first finger of an arm", "Hand holder" (catalog of orthopedic devices MPD "Ogonek", Moscow, 1998, pages 12, 13, 33).

However, it is difficult to use these devices simultaneously since each of them is suitable for autonomous use only for treatment of concrete pathologies of upper limbs.

At the present time the authors do not know an autonomous devices for restoration of bone-muscle system of upper limbs of the user as a whole.

In order to eliminate consequences of traums and operations of the waste part of the spine, a known device is widely used which is formed as a correcting corset for a waste part of the spine, provided with longitudinal metallic inserts (Catalog of orthopedic devices MPT "Ogonek", Moscow, 1998, page 29). This device during certain diseases provides a fixation of the waste part of the spine in a physiologically suitable position.

However, all above described devices are suitable only for autonomous use during the treatment of a concrete pathology of the user. These devices do not provide a possibility of their joint use in the case when such a necessity arises in view of medical conditions.

A device for treatment of patients with a deviation of stateliness and matoric activity is known from the patent of Russian Federation 2054907 with the priority 31st 1992, which is formed as a suit with mutually complimenting local motorium and dynamic elements. The local motorium elements of this suit are formed as a combination of shoulder, pelvis, knees, feet, elbows, arms and fingers supports, and are connected with one another by dynamic elements formed as elastic braces, which provide a generation of a dosed load which corrects the stateliness of the patient. Each brace is connected with two supports by connection of one of its end too one locomotorium element through a regulator of tightening and a fixed connection of its other end to another locomotorium element. Because of this connection, the location of the elastic braces relative to the body of the user is provided in accordance with preliminarily selected directions, and in particular along a front, side and rear surfaces of a patient's body. This position of the elastic braces can not be changed depending on a pathology of the user. In the case when it is necessary to change a correcting stateliness of the user, it is necessary to use another analogical device, which is formed with consideration of correction of the pathology of the user. Therefore, the above mentioned device is functionally limited.

The shoulder support of this device performs the function of an upper fixing element for fixing on it of elastic braces and an upper supporting element of the suit; the pelvic support performs the function of an intermediate support-connecting element and exhibits a loading action on the spine; the feed supports are formed as a bandage on the ankle, a harness under the arch of the foot, a harness under a front part of the foot, and performs the function of a lower fixing element for fixation on them of elastic braces of a lower supporting element of the suit, which creates a load on the body of the user; elbow and knee supports perform the functions of intermediate fixing supports, and each of them is formed as a bandage which tightly embraces an elbow/knee joint and severely limits the movability of the joint.

The above mentioned device provides a fixation of joints in desired position with the generation of a moment of a force, which enhances bending, unbending, rotation, moving forward and moving rearward of limbs and a body.

However the above described location of the elastic braces of the known device provides the formation of a locomotorium structure only of a whole suit which provides a correcting action on the body of a patient only in the even of a predetermined correspondence to the location of the elastic braces, since the fixed character of the connection of one of the ends of each corresponding brace with the corresponding support-static element limits the direction of placement of the elastic brace and exdudes a creation of a universal functional device, which is suitable for treatment of patients with different deviations of the locomotorium apparatus, including deviations of one part of the bone-muscle system.

Moreover, the above described device does not create conditions for lowering of a pathological hypertenus of large chest muscles, and correspondingly, does not allow weakening of a pathological synergy of the muscles of upper and lower limbs.

Moreover, elbow support-static element limits the bending of an arm of a user in the elbow joint and prevents widening of a physiological angle of bending, while the fixation of the lasting braces in the region of a ray-wrist joint excludes from the treatment process the work of a hand during the use of the known device, since the removing brace of the first finger can not compensate the absence of a dosed flexion and extension of the hand.

A device for treatment of patients with a damaged locomotorium apparatus, including consequences of damages of a central nervous system is known (patent of Russian Federation no. 2131232, priority Sep. 15, 1998). This device is a suit composed of mutually complementing elements, and includes a recliner for an upper part of the user's body which is formed as a supporting-placing bandage for the upper shoulder belt and a chest part of the body, formed as pelt with a height which is not less than a distance from a seventh neck vertebra to a lower edge of the user's supporting-placing bandages for lower limbs which are formed as parts placeable on these and under these; bandages for a front part of each foot, bandages for each shin-foot joint and each heel area.

The supporting-placing bandage for the shoulder belt and chest part of a body reclines the muscles of a chest part of the spine, performs the function of the supporting-placing element and participates in a creation of a single flexible carcases by connection with the bandages for one-shoulder parts. This recliner operates as a correcting device of a reflex-loading type and is a key placing element for forming of a single flexible carcases. The supporting-placing bandages for the one-shoulder parts serve for fixing to them of the fixing elements and forming of a flexible carcases for the body and lower limbs of the user.

The supporting-placing bandage for the waste performs the function of the supporting-placing element, to which flexible braces are fixed. It participates in a formation of a single flexible carcases for the body and lower limbs. The supporting-placing bandages for lower limbs are formed for fixing to them of correcting-rotation elements and participate in a formation of a single flexible carcasses for the body and lower limbs of the user. The parts on the knees are used for providing a correction of position of the knee joint relative to the pelvis-hip joint, the parts under the knees are used for providing of an additional correction of the foot and shin-foot joint. Simultaneously, the parts of the knees and the parts above the knees are not utilized.

The bandages for the front part of each foot, the bandages for each shin-foot joint and for each heel area are supporting-placing elements for forming of a single flexible carcasses in the area of the shin-foot joint end foot.

All elements of the above mentioned device are connected with one another by fixing longitudinal elements (fixing elements) which form a flexible carcasses for the body and for the limbs of the user, and also by elastic basis which perform the functions of correcting-rotating elements, and their size and location of placement can be changed in accordance with physiological and muscle synergies of the user.

The above mentioned device allows weakening and simultaneously eliminates influence of a neck symmetric tonic and labyrinthine tonic reflexes of the patient due to creation of conditions for a more complete deviation of his on-shoulder areas and there fixation in this position, which is achieved due to the use in the suit of supporting-placing bandage for the upper shoulder belt and chest part of the body or in other words the recliner. Moreover, the proposed formation of the above mentioned elements of the known device somewhat reduces, when compared with the device disclosed in the patent of Russian Federation no. 2054907, a loading action of the spine, which is favorable for the supporting-connecting apparatus of the patient.

However, the above mentioned device provides a treating action only when the suit is used as a whole. In this condition, when it is necessary to perform a treatment action only on a concrete part of the bone-muscle system of the user, it is necessary to use the device as a whole, while the use of only of its fragment in the form of the supporting-placing bandage which corresponds to the injured part does not provide a treatment action since it does not guarantee a required correction without the use of the device as a whole, which makes possible to create the pulling force of the correcting-rotating elements which is necessary for correction.

It is also necessary to mention that all known devices for treatment of patients with sequels of a central nervous system and locomotorium affection can be considered as force chains which create more or less pronounced load on all elements of the spine column without a real compensation of possible deforming effect, especially in condition that in the majority of cases the patients have a pathology of the spine column.

SUMMARY OF THE INVENTION

The main object of the present invention is, which is the basis of the present invention, to create a universal modular device, whose individual models are used for autonomous use for treatment of corresponding injured part of the bone-muscle system of the user. The other objective of the present invention which is not less important is the achievement of fixation of the correcting position of the spine of the user without the use of load on the spine.

It is another object of the present invention to restore a correct physiological position of the user's body in a space and during rest and in dynamics.

Still another object of the present invention is to remove pathological reflexes and to normalize movements of the user and also to develop organizational movements which is close to a normal one.

This and other objects are achieved by providing a device for user's with sequels of central nervous system affections and/or locomotorium affection of a body, which includes a recliner located in an upper area of the above mentioned user's body and attachments for moving apart of on-shoulder parts and moving shoulder blades to the spine; means for correcting of medium area of the user's body located in the region of a waste, means for correcting a hip and a shin of a lower extremity formed with a possibility of fixing of the above mentioned hip and shin and a predetermined position, means for correcting of shin-foot joint and fingers of a lower extremity, formed with the possibility of fixing of a foot of the above mentioned lower extremity relative to the shin-foot joint, a plurality of correcting-rotating elements and a plurality of connecting elements, wherein in accordance with the present invention the above mentioned elements are formed as a plurality of modules which cover certain parts of the user's body and each of which is formed with the possibility of a separate use and which include a recliner performing the functions of a first of the above mentioned modules; means for correcting of the medium area of the above mentioned user's body which performs the function of the second of the above mentioned plurality of modules and is suitable for correcting of the spine without a vertical load; at least one means for correcting of a hip and a shin of a lower extremity of the above mentioned user's body which performs the function of a third from the above mentioned plurality of modules and is formed with the possibility of fixing of the above mentioned hip and shin in a predetermined position with providing at the same time a freedom of movement of the knee joint of the above mentioned lower extremities; at least one means for correcting of a shin-foot joint and fingers of the lower extremity of the above mentioned user's body which performs the function of a fourth from the above mentioned plurality of modules which is formed with the possibility of fixing of the foot of the above mentioned lower extremity relative to the shin-foot joint in a frontal and sagital planes with providing a freedom of movement of the shin-foot joint; an exterior surface of each of the above mentioned plurality of modules is composed of a material which has a nap which is suitable for the use of a connection of the Velcro type; a plurality of correcting-rotating elements which successively connect of the above mentioned second, third and fourth modules so that they can be disconnected; each of the above mentioned plurality of correcting-rotating elements is formed as a band of elastic material with a relative stretching of 5–50% and provides a correctional movement of the user during its displacement; a plurality of connecting means provided on each of the above mentioned plurality of correcting-rotating elements which regulate the stretching of the above mentioned correcting rotating elements in each location of their connection with each of the above mentioned second, third, and fourth modules; each of the above mentioned plurality of means for connection have an engaging surface suitable for providing a connection of the Velcro type with the above mentioned outer surface of each of the above mentioned second, third, and fourth modules in any location of the surface depending on a pathology of the user.

It is advisable that each correcting-rotating element have a means for changing of its length.

It is advantageous when the above mentioned recliner includes a first flexible band and a second flexible band, each having a first end and a second end; each of the above mentioned first and second flexible bands is formed as spatially curved in form of a loop so that a first strap and a second strap are formed, each embracing a corresponding shoulder joint of the above mentioned user's body; means of interaction which connect the above mentioned first ends of the above mentioned first and the above mentioned flexible bands with the possibility of regulation of a distance between them and located on the back of the above mentioned user's body; the above mentioned second end of the above mentioned first flexible band is fixedly connected to the above mentioned first flexible band near the above mentioned first means of interaction; the above mentioned second end of the above mentioned second flexible band is fixedly connected to the above mentioned second flexible band near the above mentioned first means of interaction.

It is desirable that the device contains an elastic plate which covers a portion of the above mentioned user's back in the zone of shoulders, located between the recliner and the back of the user; the outer surface of the above mentioned plate is composed of a material which has nap suitable for the use of the Velcro-type connection and provided for connection of the above mentioned first and second straps of the above mentioned recliner; inner side of each of the above mentioned first and second straps have an engaging surface for providing a connection of the Velcro type with the above mentioned outer surface of the above mentioned plate; a connecting means arranged on the lower part of the above mentioned flexible plate and provided for connection with the above mentioned second module.

It is favorable when the above mentioned means for correction of the medium part of the above mentioned user's body contains a corset which has a complicated profiled shape providing a correction of the above mentioned spine without the vertical load, a first part of the above mentioned corset embraces the above mentioned user's body in the area of the above mentioned waste and has means for fixing of this part on the above mentioned user's body in a transverse direction; a second part of the above mentioned corset which covers the above mentioned back in the zone of shoulder blades.

It is advisable when the above mentioned means of correction of the medium area of the above mentioned user's body includes corset which has a complicated profiled shape which provides correction of the above mentioned spine without a vertical load and embraces the above mentioned user's body in the area of the above mentioned waste and has means for its fixation on the above mentioned user's body in a transverse direction; connecting means form with the possibility of connection with the above mentioned connecting means of the above mentioned flexible spring.

It is possible that the above mentioned means for connecting a hip and shin of the above mentioned lower extremity connect a first flexible bandage which embraces the above mentioned lower extremity above its knee joint and has a first end, a second end and a transverse edge which has a medium part; a second flexible bandage which embraces the above mentioned lower surface under the above mentioned knee joint and has a first end, a second end and a transverse edge located opposite to the above mentioned longitudinal edge of the above mentioned first flexible bandage and has a medium part, connected with the above mentioned medium part of the above mentioned longitudinal edge of the above mentioned first flexible bandage; a location of connection of the above mentioned medium part of the above mentioned opposite longitudinal edges of the above mentioned first and second flexible bandages is located in the area under the knee of the above mentioned lower extremity, first means of interaction which connects the above mentioned first end and the above mentioned second end of the above mentioned first flexible bandage for its fixation above the above mentioned knee joint with the possibility of regulation of a distance between the above mentioned ends: a second means of interaction which connects the above mentioned first end and the above mentioned second end of the above mentioned second flexible bandage for its fixation under the above mentioned knee joint with the possibility of regulation of distance between the above mentioned ends.

It is possible that the above mentioned means for correction of the shin-foot joint and fingers of the above mentioned lower extremity contain a first flexible belt which embraces the ankle of the above mentioned lower extremity and has a first end and a second end; and means of interaction for fixing of the above mentioned first flexible belt on the above mentioned ankle which connects the above mentioned first end and the second end of the above mentioned first flexible belt with the possibility of regulating a distance between these ends; a second flexible belt which embraces the above mentioned foot of the above mentioned lower extremity in the zone of its longitudinal arch and has a first end, a second end and a lower surface facing toward the above mentioned foot; the above mentioned first and second ends of the above mentioned second flexible belt connected to the above mentioned first flexible belt from the opposite lateral sides of the above mentioned ankle; a cap-sole element of a cross-shape which has a first, second, third and fourth ends on each of the above mentioned first, second and third ends there are fixing elements; the above mentioned first, second and third ends are spatially bent toward one another and embrace the above mentioned foot in the area of a cap of the above mentioned lower extremity and connected by the above mentioned fixing elements; the above mentioned fourth end is formed free and located under the above mentioned foot along its whole length; two elastic braces each connecting correspondingly the above mentioned first and the above mentioned second flexible belts with the above mentioned cap-sole element and the above mentioned area of the cap with the possibility of regulating of a distance between them.

It is desirable that the device also contains a plurality of placing-connecting means for connection of the above mentioned plurality of the correcting-rotation elements with the corresponding one of the above mentioned plurality of modules; each of the above mentioned plurality of the placing-connecting means includes two layers; an outer surface of first of the layers is formed from a material which has a nap suitable for a Velcro-type connection; an outer surface of the second layer is formed as engaging and suitable for the use of the Velcro-type connection; at least one strap fixedly connected on each of the above mentioned plurality of the placing-connecting means; each of the above mentioned plurality of the connecting means has on each of the above mentioned correcting-rotating elements has a nap surface suitable for a Velcro-type connection. It is advisable when the device contains at least one means for correction of an upper extremity of the above mentioned user-s body which performs the function of a fifth of the above mentioned plurality of modules, formed with the possibility of fixing of shoulder and fore shoulder of the above mentioned upper extremity in the predetermined position with providing of a freedom of movement of the elbow joint of the above mentioned upper extremity. An outer surface of the above mentioned fifth module is formed from the material which has a nap suitable for the use of a Velcro-type connection; at least one correcting-rotating element of the above mentioned means of correction of the upper extremity each connects the above mentioned fifth modules with the above mentioned first module with the possibility of their disconnection; the above mentioned correcting-rotating element of the above mentioned means for correction of the upper extremity is formed as a band from an elastic material with relative stretching of 5–50% and provides a correctional movement of the above mentioned upper extremity during its operation; and means of connection provided on the above mentioned correcting-rotating element of the above mentioned means for correction of the upper extremity, which regulates the tightening of the above mentioned correcting-rotating element at a location of its connection with each of the above mentioned first and fifth modules and has an engaging surface suitable for providing a Velcro-type connection at any location of the above mentioned outer surfaces of the above mentioned first and second modules depending on the pathology of the user. It is desirable that each of the above mentioned correcting-rotating elements of the above mentioned means for correction of the upper extremity has a means for changing of its length.

It is useful when the above mentioned means for correction of the above mentioned upper extremity has a first spatially curved flexible strip which embraces the above mentioned upper extremity under its above mentioned elbow joint and has a first end, a second end and a longitudinal edge having a medium part; a second spatially curved flexible strip which embraces the above mentioned upper extremity under the above mentioned elbow joint and has a first end, a second end and a longitudinal edge located opposite to the above mentioned longitudinal edge of the above mentioned first strip and having a medium part fixedly connected with the above mentioned medium part of the above mentioned longitudinal edge of the above mentioned first flexible strip; a location of the fixed connection of the above mentioned medium part of the above mentioned opposite longitudinal edges of the above mentioned first and second flexible strips is located in an under-elbow area of the above mentioned upper extremity; a first means of interaction which connects the above mentioned first end and the above mentioned second end of the above mentioned first flexible strip for fixation of the above mentioned first flexible strip above the above mentioned elbow joint with the possibility of a regulation of the distance between the above mentioned ends; a second means of interaction which connects the above mentioned first end and the above mentioned second end of the above mentioned second flexible strip of the above mentioned bandage of a shoulder and the fore shoulder for fixation of the above mentioned second flexible strip above the above mentioned elbow joint with the possibility of regulation of a distance between the above mentioned ends; a hand flexible element which is ergonomically suitable for fixing on a pump and deflecting of a thumb of the above mentioned upper extremity and having a V-shaped, a first end and a second end, each of which has a means for fixation on the hand of the above mentioned upper extremity with the possibility of regulation of a tightening of force of the above mentioned hand flexible element; at least one elastic brace which connects the above mentioned hand flexible element with the above mentioned second flexible strip and has a first end and a second end; and means for connecting having provided on each of the above mentioned first and second ends of the above mentioned elastic brace which regulates a tightening of the above mentioned elastic brace in the location of its connection of the above mentioned hand flexible element and the above mentioned second flexible element.

The above mentioned construction of the proposed device provides the formation of a universal modular device, whose separate modules are suitable for autonomous use during treatment of corresponding injured part of a bone-muscle system of the user or its central nervous system.

Moreover, the device provides obtaining of fixation of the corrected position of the spine of the user without the use of a vertical load on the spine. At the same time there is a possibility of a restoration of a correct physiological position of the user's body in a space and in a rest condition and in autonomic condition, and also it is possible to reduce pathological reflexes and to normalize movements of the user and develop organization of movement of the user which is close to a normal one. At the same time the construction of each of the above mentioned modules can be different from the above described and can have a different use which is suitable for analogous purposes. However, the above mentioned objectives can be efficiently achieved with the use of a device for the user's sequels of central nervous system and locomotorium affection of the body, which has:

A plurality of modules which cover certain areas of the user's body and each form with a possibility of a separate use; a recliner which performs the function of the first of the above mentioned plurality of modules and located in the upper area of the users body and suitable for spreading of above shoulder areas and moving of the shoulder blades toward the spine; the above mentioned recliner contains a first flexible band and a second flexible band each having a first end and a second end; each of the above mentioned first and second flexible bands is formed as a spatially curved band in form of a loop so that a first strap and a second strap are formed, each embracing a corresponding shoulder joint of the above mentioned user's body; and means for interaction which connects the above mentioned first and the above mentioned second flexible bands with the possibility of regulation of a distance between them and located on a back of the users body; the above mentioned second end of the above mentioned first flexible band is fixedly connected to the above mentioned first flexible band near the above mentioned first means of interaction; the above mentioned first end of the above mentioned second flexible band which is fixedly connected to the above mentioned second flexible band near the above mentioned first means of interaction; and means for correction of a medium area of the above mentioned user's body which performs the function of the second of the above mentioned plurality of modules and located in the area of waste and suitable for correction of the above mentioned spine without a vertical load; and means for correcting of a medium area of the above mentioned user's body which includes a corset having a complicated profiled shape which provides a correction of the above mentioned spine without a vertical load; a first part of the above mentioned corset embraces the above mentioned user's body in the area of waste and have a means for fixing of this part of the above mentioned users body in a transverse direction; a second part of the above mentioned corset covering a back of the above mentioned users body in the zone of shoulders; at least one means for correction of a hip and shin of lower extremity of the above mentioned users body which performs the function of a third of the above mentioned plurality of modules and formed with the possibility of fixing of the above mentioned hip and shin in the predetermined position with providing a freedom of movement of a knee joint of the above mentioned lower extremity; the above mentioned means for correction of the hip and shin of the above mentioned lower extremity of the above mentioned user's body contains a first flexible bandage which embraces the above mentioned lower extremity above its above mentioned knee joint and having a first end, a second end and a longitudinal edge having a medium part; a second flexible bandage which embraces the above mentioned lower extremity under the above mentioned knee joint and has a first end, a second end and a longitudinal edge located above the above mentioned longitudinal edge of the above mentioned first bandage and having a medium part fixedly connected with the above mentioned medium part of the above mentioned longitudinal edge of the above mentioned first flexible bandage; a location of the fixed connection of the above mentioned medium parts of the above mentioned opposite longitudinal edges of the above mentioned first and second flexible bandage is located in an area under the knee of the above mentioned lower extremities; a first means of interaction which connects the above mentioned first end and the above mentioned second end of the above mentioned first flexible bandage for its fixation above the above mentioned knee joint with the possibility of regulation of the distance between the above mentioned ends; a second means of interaction connecting the above mentioned first end and the above mentioned second end of the above mentioned second flexible bandage for its fixation above the above mentioned knee joint with the possibility of regulation of a distance between the above mentioned ends; at least one means for correction of a shin-foot joint and fingers of the lower extremity of the above mentioned user's body which forms the function of a fourth from the above mentioned plurality of modules and formed with the possibility of fixing of the foot of the above mentioned lower extremity relative to the shin-foot joint in a frontal and sagittal planes with providing a freedom of movement of the shin-foot joint of the above mentioned lower extremities; the above mentioned means for correction of the shin-joint foot and fingers of the above mentioned lower extremity includes a first flexible belt which embraces an angle of the above mentioned lower extremity and has a first end and a second end; and means for interaction for fixing of the above mentioned first flexible belt on the above mentioned ankle and connecting the above mentioned first end and second end of the above mentioned first flexible belt with the possibility of regulation of a distance between these ends; a second flexible belt which embraces the above mentioned foot of the above mentioned lower extremity in the zone of its longitudinal arch and has a first end and a second end; the above mentioned first and second ends of the above mentioned second flexible belt are fixed to the above mentioned first flexible belt from the opposite lateral sides of the above mentioned angle; a cap-under sole element having a cross-shape and having a first, second, third and fourth ends, with fixed elements provided on the above mentioned first, second and third ends; the above mentioned first, second and third ends are spatially curved toward one another and embrace the above mentioned foot in the area of the cap of the above mentioned lower extremity and connected by the above mentioned fixing elements; the above mentioned fourth end is formed free and located under the above mentioned foot along all its length; two elastic braces each connecting correspondingly the above mentioned first and the above mentioned second flexible belts with the above mentioned cap-undersole element in the above mentioned area of the cap with the possibility of regulation of a distance between them; the outer surface of each of the above mentioned plurality of modules is formed of a material having a nap which is suitable for the use of a Velcro-type connection; a plurality of correcting-rotation elements which consecutively connect of the above mentioned second, third, and fourth modules with the possibility of their disconnection; each of the above mentioned plurality of correcting-rotating elements is formed as a band of an elastic material with a relative stretching 5–50% and providing a correction of the user's movement during its displacement; a plurality of means for connection on each of the above mentioned plurality of the correcting-rotating element which regulate a tightening of the above mentioned correcting-rotating elements in each place of their connections with each of the above mentioned second, third and fourth modules; each of the above mentioned plurality of the means for connection have an engaging surface suitable for providing a Velcro-type connection with the above mentioned outer surface of each of the above mentioned second, third and fourth modules in any place of this surface, depending on the pathology of a user. It is advisable when each of the correcting-rotating elements has a means for changing of its length.

It is useful when the device has at least one means for correcting of the upper extremity of the above mentioned user's body which performs the function of a fifth of the above mentioned plurality of modules and is formed with a possibility of fixing of a shoulder and fore-shoulder of the above mentioned upper extremity in the predetermined position with providing a freedom of movement of an elbow joint of the above mentioned upper extremity, wherein the above mentioned means for correction of the above mentioned upper extremity includes a first spatially curved flexible band which embraces the above mentioned upper extremity above its above mentioned elbow joint and having a first end, a second end a longitudinal edge having a medium part, a second spatially curved flexible band which embraces the above mentioned upper extremity under the above mentioned elbow joint and has a first end, a second end and a longitudinal edge located opposite to the above mentioned longitudinal edge of the above mentioned first flexible strip and having a medium connected with the above mentioned medium part of the above mentioned longitudinal edge of the above mentioned first flexible strip; a place of connection of the above mentioned medium parts of the above mentioned medium parts of the above mentioned opposite longitudinal edges of the above mentioned first and second flexible strips is located in an under-elbow area of the above mentioned upper extremities; a first means of interaction which connects the above mentioned first end and the above mentioned second end of the above mentioned first flexible strip for fixing of the above mentioned first flexible strip above the above mentioned elbow joint with the possibility of regulation of a distance between the above mentioned ends; and second means for interaction which connects the above mentioned first end and the above mentioned second end of the above mentioned first flexible strip of the above mentioned bandage of shoulder and fore shoulder for fixing of the above mentioned second flexible strip under the above mentioned elbow joint with the possibility of regulation of a distance between the above mentioned ends; a hand flexible element which is ergonomically suitable for fixing on a pump and moving of a thumb of the above mentioned upper extremity and having a V-shape, a first end and a second end each of which has a means for fixation on the palm of the above mentioned upper extremity with the possibility of regulation of the tightening force of the above mentioned hand flexible element; at least one elastic brace which connects the above mentioned hand flexible element with the above mentioned second flexible strip and has a first end and a second end; and means for connecting provided on each of the above mentioned first and second above mentioned elastic brace and regulating a tightening of the above mentioned elastic brace in the place of its connection with the above mentioned hand flexible element and the above mentioned second flexible strip; analogous surface of the above mentioned fifth module formed from the material having a nap suitable for a Velcro-type connection; at least one correcting-rotation element of the above mentioned means for correction of the upper extremity which connects the above mentioned fifth module with the above mentioned first module with the possibility of their disconnection, the above mentioned correcting-rotating element of the above mentioned means for correcting of the upper extremity is formed as a band from an elastic material with a relative stretching of 5–50% and provides a correction of movement of the above mentioned upper extremity during its operation; and means for connection provided on the above mentioned correcting-rotation element of the above mentioned means for correction of the upper extremity and regulating a tightening of the above mentioned correction-rotation element in the place of its connection with each of the above mentioned first and fifth modules and having an engaging surface suitable for providing a Velcro-type connection in any place of the above mentioned outer surfaces of the above mentioned fifth and first modules depending on the pathology of the user.

It is desirable that each of the above mentioned correcting-rotation elements of the above mentioned means for correction of the upper extremity has a means for changing of its length.

At the same time the above mentioned objectives can be achieved in a most efficient way by locating of a device for users with sequels of central nervous system and/or locomotorium affection of a body which includes a plurality of modules covering certain areas of the user's body each of which is formed with the possibility of a separate use; a recliner performing the function of a first of the above mentioned modules and located in the upper area of the above mentioned user's body and suitable for moving a part of above-shoulder area and moving the shoulder blades toward the spine, wherein the above mentioned recliner includes a first flexible band and a second flexible band each having a first end and a second end; each of the above mentioned first and second flexible bands is formed spatially curved as a loop such that a first strap and a second strap are formed, each embracing a corresponding shoulder joint of the above mentioned user's body; and means for interaction connecting the above mentioned first ends of the above mentioned first and the above mentioned second flexible bands with the possibility of regulation of a distance between them as located on a back of the above mentioned user's body; the above mentioned second end of the above mentioned first flexible band is fixedly connected on the above mentioned first flexible band near the above mentioned first means of interaction; the above mentioned second end of the above mentioned second flexible band is fixedly connected on the above mentioned second flexible band near the above mentioned first means of interaction; and means for correction of a medium area of the above mentioned user's body which performs the function of a second of the above mentioned modules and is located in the area of a waste and suitable for correction of the above mentioned spine without a vertical load; and the above mentioned means for correction of the medium area of the above mentioned user's body includes a corset having a complicated profiled shape which provides a correction of the above mentioned spine without the vertical load; a first part of the above mentioned corset embraces the above mentioned user's body in the area of the above mentioned waste and has a means for fixing of this part on the above mentioned user's body in a transverse direction; a second part of the above mentioned corset covers a back of the above mentioned user's body in the zone of shoulder blades; at least one means for correction of a hip and shin of the lower extremity of the above mentioned user's body performs the function of the third of the above mentioned plurality of modules and is formed with a possibility of fixing of the above mentioned hip and shin in a predetermined position is providing a freedom of movement of the above mentioned knee joint of the above mentioned lower extremity, wherein the above mentioned means for correction of hip and shin of the above mentioned lower extremity includes a first flexible bandage which embraces the above mentioned lower extremity above the above mentioned knee joint and has a first end, a second end and a longitudinal edge having a medium part; a flexible bandage which embraces the above mentioned lower extremity under the above mentioned knee joint and has a first end, a second end and a longitudinal edge located opposite to the above mentioned longitudinal edge of the above mentioned first flexible bandage and has a medium part fixedly connected with the above mentioned medium part of the above mentioned longitudinal edge of the above mentioned first flexible bandage; a place of fixed connection of the above mentioned medium parts of the above mentioned opposite longitudinal edges of the above mentioned first and second flexible bandages is located in an under-knee area of the above mentioned lower extremity; the first means of interaction connects the above mentioned first ends and the above mentioned second end of the above mentioned first flexible bandage for its fixation above the above mentioned knee joint with the possibility of regulation of a distance between the above mentioned ends; second means for interaction which connects the above mentioned first end and the above mentioned second end of the above mentioned second flexible bandage for its fixation under the above mentioned knee joint with the possibility of regulation of distance between the above mentioned ends; at least one means of correction of the shin-foot joint and fingers of the lower extremity of the above mentioned user's body which performs the function of fourth of the above mentioned plurality of modules and is formed with the possibility of fixation of the foot of the above mentioned lower extremity relative to the shin-foot joint in a frontal and sagittal surfaces with the possibility of a movement of freedom of the shin-foot joint, and the above mentioned means of correction of the shin-foot joint and fingers of the above mentioned lower extremities includes a first flexible belt which embraces an ankle of the above mentioned lower extremity and has a first end and a second end; and means for interaction for fixing of the above mentioned first flexible belt on the above mentioned ankle and connects the above mentioned first and the above mentioned second end of the above mentioned first flexible belt with the possibility of regulation of a distance between these ends; a second flexible belt which embraces the above mentioned foot of the above mentioned lower extremity in the zone of its longitudinal arch and has a first end and a second end; the above mentioned first and second ends of the above mentioned second flexible belt are fixed to the above mentioned first flexible belt from the opposite lateral sides of the above mentioned ankle; a cap-sole element having a cross shape and a having a first, second, third and fourth ends with fixing elements on each of the above mentioned first, second and third ends; the above mentioned first, second and third ends are spatially curved toward one another and embrace the above mentioned foot in the area of the cap of the above mentioned lower extremity and are connected by the above mentioned fixing elements; the above mentioned fourth end is formed free and located under the above mentioned foot along its whole length, two elastic braces each connecting correspondingly the above mentioned first and the above mentioned flexible belts with the above mentioned cap-sole element in the above mentioned area of the cap with the possibility of regulation of distance between them; at least one means of correction of the upper extremity of the above mentioned user's body which performs the function of the fifth of the above mentioned plurality of modules and formed with the possibility of fixing of a shoulder and fore shoulder of the above mentioned upper extremity in a predetermined position with providing a freedom of movement of the elbow joint of the above mentioned upper extremity, with the above mentioned means for correction of the above mentioned upper extremity containing a first spatially curved flexible strip which embraces the above mentioned upper extremity above the above mentioned elbow joint and having a first end, a second end and a longitudinal edge having a medium part; a second spatially curved flexible scrip which embraces the above mentioned upper extremity under the above mentioned elbow joint and having a first end, a second end and a longitudinal edge located opposite to the above mentioned longitudinal edge of the above mentioned first flexible strip and having a medium part connected with the above mentioned medium part of the above mentioned longitudinal edge of the above mentioned flexible strip; a place of connection of the above mentioned medium parts of the above mentioned opposite longitudinal edges of the above mentioned first and second flexible strips is located in an under elbow area of the above mentioned upper extremity; a first means of interaction connecting the above mentioned first end and the above mentioned second end of the above mentioned first flexible strip for fixation of the above mentioned first flexible strip above the above mentioned elbow joint with the possibility of regulation of a distance between the above mentioned ends; a second means of interaction connecting the above mentioned first end and the above mentioned second end of the above mentioned second flexible strip of the above mentioned band-shoulder and fore shoulder for fixing an above mentioned second flexible strip under the above mentioned elbow joint with the possibility of regulation of a distance between the above mentioned ends; a hand flexible element ergonomically suitable for fixing on the palm and moving of a thumb of the above mentioned upper extremity and having a V-shape, a first end and a second end each having a means for fixation on the palm of the above mentioned upper extremity with a possibility of regulation of a tensioning force of the above mentioned canned flexible element; at least one elastic brace connecting the above mentioned hand flexible element with the above mentioned second flexible strip and having a first end and a second end; means for connecting provided on each of the above mentioned first and second ends of the above mentioned elastic brace and regulating a tensioning of the above mentioned elastic brace in the place of its connection with the above mentioned hand flexible element and the above mentioned second flexible strip; an outer surface of each of the above mentioned plurality of modules is formed from a material having a nap suitable for the use of a Velcro-type connection; a plurality of correcting-rotating elements consecutively connecting the above mentioned second, third and fourth modules with the possibility of their disconnection and the above mentioned fifth module with the above mentioned first module with the possibility of their disconnection; each of the above mentioned plurality of correcting-rotation elements is formed as a band of an elastic material with a relative stretching of 5–50% and providing a correction movement of the user during its displacement and/or operation; a plurality of means for connection provided on each of the above mentioned plurality of the correcting-rotation element and regulating a tightening of the above mentioned correction-rotating element in each place of their connection with each of the above mentioned plurality of modules; each of the above mentioned plurality of means for connection having an engaging surface suitable for providing a Velcro-type connection in any place of the above mentioned outer surfaces of which of the above mentioned plurality of modules depending on the user's pathology.

It is advantageous when each of the above mentioned correcting-rotation elements has a means for changing of its length.

The present invention provides condition for fixing of a spine of the user in a creped position, and also for its unloading and traction during diagnostics in the patient of a paralytic scoliosis the thickness of Sheirmann-may a traumatic injury of bodies of vertebra in condition of a typical "round" back, a child cerebral paralysis, osteokhondrosis of spine and other analogous diseases.

The proposed device, due to the performed mechanical pulling correction without the use of load on the spine, contributes to removal of action of late-tonic reflexes due to movement apart of the on-shoulder areas and stabile fixation in this position. The proposed invention provides a reflectoric reduction of a pathological tonus of chest muscles and muscles of pelvic and shoulder belts, reflectoric reduction of a tonus of lower extremities and therefore provides a possibility of parting and fixing of maximum physiological position of upper and lower extremities in shoulder, elbow, ray-wrist, pelvic-hip, knee, shin-foot joints and joints of foot in a movable condition and in dynamics. Moreover, the proposed invention provides normalization of tonus of muscles and increase of a muscle force and perseverance which can be qualified as a result of training function of the new device.

The proposed invention does not provide a single flexible carcasses for the user's body and therefore eliminates all above mentioned negative results when it is provided. At the same time each module of the proposed invention performs its function to achieve the proposed objectives, for example the recliner formed in accordance with the present invention is used for forming of a correct stateliness, the correcting corset which is formed in accordance with the present invention provides a correction of spine without the use of the load on it, the complex bandage of hip and shin and correcting attachments for the shin-foot joint and toes of a foot in accordance with the present invention and make possible the use of other known correcting attachments simultaneously with the proposed device.

In order to expand the functional possibilities of the proposed invention, in particular for treating of patients for example after a stroke and a child cerebral paralysis with spastic tonus of muscles of upper extremities, the device has the fifth module which is connected with the first module by at least one correcting-rotation element. The construction of the fifth module makes possible simultaneously to correct pathology of the whole upper extremity, with preserving of the freedom of movement of the elbow joint.

In order to expand functional possibilities of the proposed device and in particular for treatment of for example of patients with skull brain trauma or trauma of various parts of spine the proposed device can have a means for locating in the area of chest and/or a means for locating in the area of forehead and/or a means which is a device for correcting of a neck part of the spine. The presence of the means for changing a length of each correcting-rotation element makes possible to use the same device for various age groups of the user's, and also to increase or to reduce a load during the use of the device.

The band of the recliner can have a different width, including the width sufficient for forming a vest.

In accordance with the present invention the outer surface of structural components composed of a material which corresponds to the first surface of the Velcro, and each fixing element has the surface forming the opposite surface of the Velcro connection. This structural solution provides a universality of the proposed device and makes possible its use for treatment of great number of various pathologies, and during the positive treatment results from moving the device, makes possible a change of position of individual modules and elements of the modules relative to one another, depending on the course of the thickness and the presence of a treatment effect, so that it is possible to use various treatments the same device without the use of other devices, which substantially increases its functional possibilities. The proposed device can be used together with other know orthopedic means, the correct position for example of toes of legs and fingers of arms, or neck, or head.

The use of the proposed invention makes possible a correction which has a complex nature including a combination of the lowering of the load of the spine and creating of correcting dosed loads directed to the upper and lower extremities.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 5 is a view showing the proposed device for treatment of patients with an impaired function of lower extremities in accordance with the present invention with perspective;

FIG. 6 is a view showing is a view showing the proposed device for treatment of patients with impaired function of upper extremities, in accordance with the present invention;

FIG. 7 is a view showing the inventive device for treatment of patients with impaired function of muscles of the shoulder belt, in accordance with the present invention;

FIG. 8 is a view showing variants of fixation of correcting-rotation elements to an outer surface of each module in accordance with the present invention; and FIG. 9 is a view showing a correcting-rotation element with means for changing of its length, in accordance with the present invention.

DESCRIPTION OF THE PREFERRED EMBODIMENTS

Figure 1:
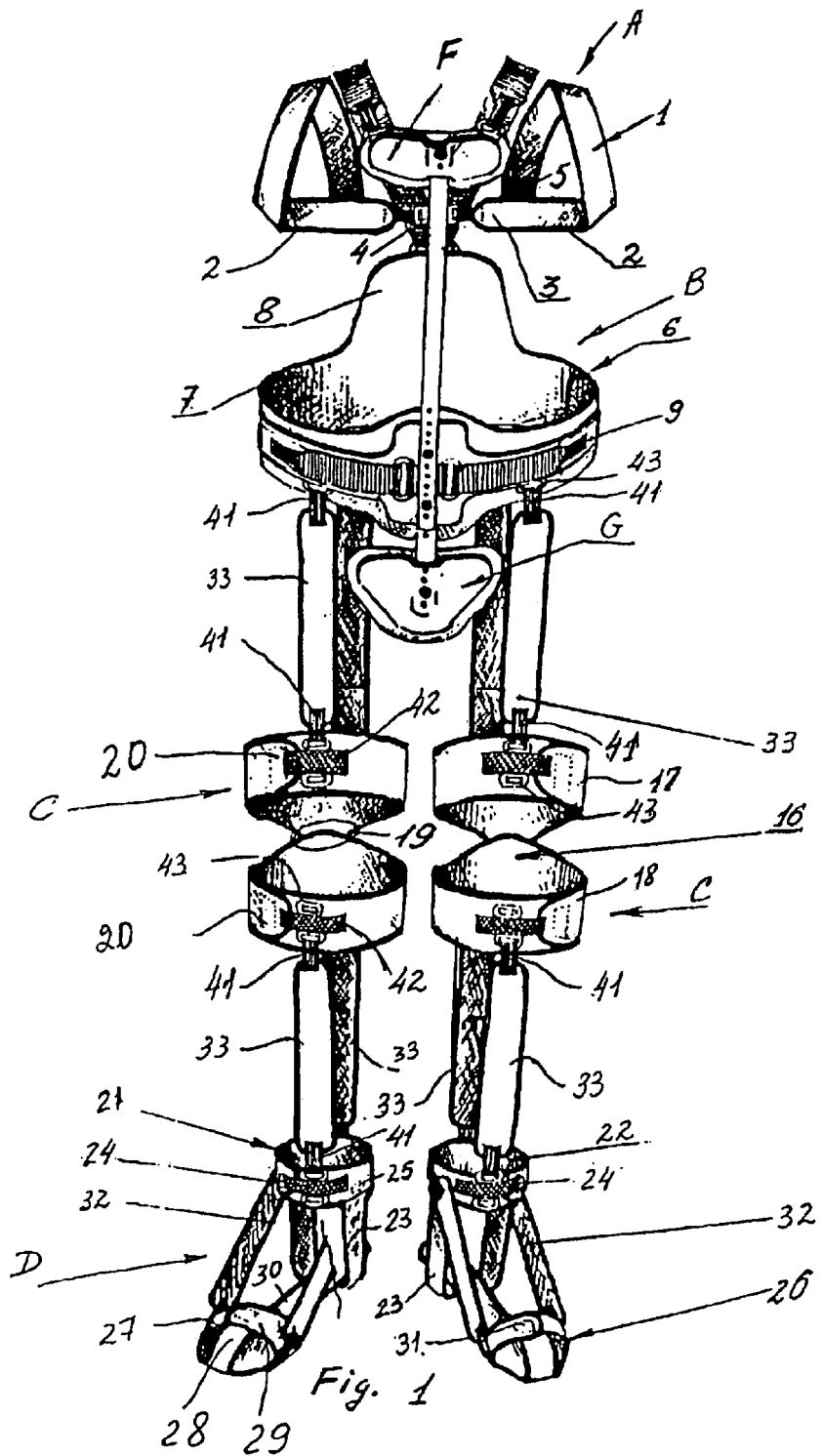
FIG. 1 is a view showing a proposed device in a perspective in accordance with the first embodiment.
Figure 2:
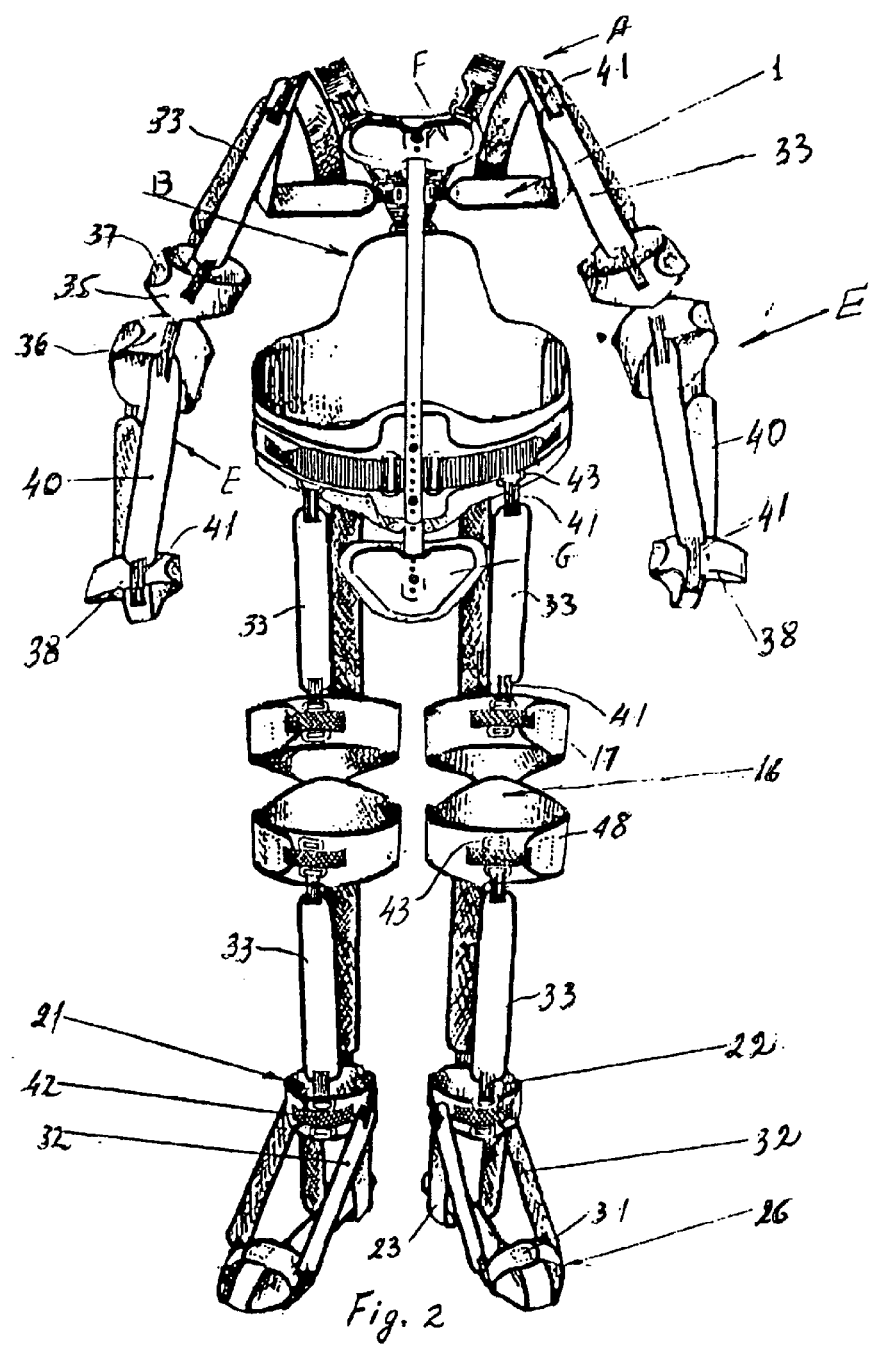
FIG. 2 is a view showing the proposed device in perspective, in accordance with the second embodiment.

The proposed device for treatment of patients with sequels of central nervous system and/or locomotoric affection in accordance with present invention has individual modules A, B, C, D, E, shown in FIGS. 1, 2, 3, 4, and formed with the possibility of individual (autonomous) use, and do not resume a formation of a single flexible carcasses with the user's body (the user is not shown in the drawing).

The first module A performs a reclining of a shoulder belt of the user, in other words forming of a correct stateliness. It forms as a recliner 1 shown in FIGS. 1, 2, 3, for an upper area of the user's body, which includes a first and a second flexible bands 2 each having a first end 3 connected by fixing elements 4 with the possibility of regulation of a distance between them and located on a back of the user. The fixing elements 4 can be known fixing elements proposed for the analogous purposes for example as a catch. Each of the flexible bands 2 is formed as a spatially curved band in form of a loop, and the second ends 5 of each flexible band 2 are fixedly connected on the band 2 near the fixing elements 4 so as to form a first and second straps each embracing a corresponding shoulder joint of the user's body. Each flexible band 2 of the recliner 1 can have a width sufficient for forming a vest.

The second module B is formed as a means for correction of a medium area of the user's body and located in the area of waste and suitable for correction of spine without a vertical load. The proposed means for correction of the medium area of the user's body is formed as a corset 6 which has a complicated profiled shape providing correction of the spine without the load. The corset 6 has a first part 7 which embraces a user's body in the area of waste, and a second part 8 which covers the back in the zone of shoulder blades of the user. The above mentioned parts 7 and 8 are formed of one piece with one another. The first part 7 has means 9 for its fixing on the user's body in a transverse direction. In another embodiment the proposed means for correction of the medium area of the user's body can have only one part 10 shown in FIG. 4, which is formed as a corset 1 having a complicated profiled shape which provides correction of spine without a vertical load. It embraces the above mentioned users body in the area of waste and has means 12 for its fixing on the users body in a transverse direction.

The device can have a flexible plate 13 which covers the portion of the back of the user in the zone of shoulder blades located between the recliner 1 and the back of the user. The outer surface of the plate 13 is composed of a material which has a nap suitable for the use of Velcro-type connection and provided for connection of the first and second straps of the recliner 1, with an engaging surface of the inner side of each of them provided for a Velcro-type connection of the above mentioned outer surface of the above mentioned plate 13. In the lower part of the flexible plate 9, there is a connecting means 14 for connection with the above mentioned second module B which must have a connecting means 15 connectable with the connecting means 14 of the flexible spring 13.

The corset can be formed of any known construction for a correction of the spine without the use of a vertical load, for example a "bekker" corset.

The proposed device, depending on the pathology of the user, can have means F to be located in the area of chest and/or means G for location in the area of forehead and/or means which forms the wiper correction of a neck part of the spine (not shown in the drawing).

The third module C is at least one means 16 for correction of hip and shin of the upper extremity of the user's body. It is formed with the possibility of fixing of the above mentioned hip and shin in the predetermined position as providing a freedom of movement of the knee joint of the above mentioned lower extremity. When the user have a pathology of both lower extremities, two such modules can be provided. The means 13 for correction of hip and shin of the above mentioned lower surface of the users body includes a first flexible bandage 17 which embraces the above mentioned lower extremity above the knee joint and has a first end, a second end and a longitudinal edge having a medium part; a second flexible 18 which embraces the lower extremity under the above mentioned knee joint and having a first end, a second end and a longitudinal edge located opposite to the above mentioned longitudinal edge of the first place bandage 17 and having a medium part connected with the above mentioned medium part of the longitudinal edge of the first flexible bandage 17, a location 19 of connection of the above mentioned medium parts of the opposite longitudinal edges of the first and second flexible bandage 17, 18 located in the under-knee area of the above mentioned lower extremities; a first means of interaction connecting the above mentioned first end and the above mentioned second end of the first flexible bandage 17 for its fixation above the knee joint with the possibility of regulation of a distance between the above mentioned ends; a second means 20 of interaction connecting the above mentioned first end and the second end of the above mentioned second flexible bandage 18 for its fixation under the above mentioned knee joint with the possibility of regulation of a distance between the above mentioned ends.

The fourth module D is at least one means 21 for correction of shin-foot joint and toes of the lower extremity of the above mentioned user's body. It is formed with a possibility of fixing of a foot of the above mentioned lower extremity relative to the shin-foot joint in frontal and sagittal surfaces with the freedom of movement of the shin-foot joint. When the user has pathology of both lower extremities there should be two modules D.

The means 21 for correction of the shin-foot joint and toes of the above mentioned lower extremity includes a first flexible belt 22 which embraces an ankle of the lower extremity and has a first end and has a first end and a second end, a second flexible belt 23 which embraces the foot of the above mentioned lower extremity in the zone of its longitudinal arch and has a first end and a second end; means 24 of interaction for fixing the above mentioned first flexible belt 22 on the ankle and connecting the first end and the second end of the first flexible belt 22 with the possibility of regulation of a distance between these ends; the above mentioned first and second ends of the second flexible belt 23 are fixed by fixing elements 25 to the first flexible belt 22 from the opposite lateral sides of the ankle; a cap-sole element 26 having a cross-shape and a first, second, third and fourth ends 27, 28, 29, 30. Fixing elements 31 are located on each of the first, second and third ends 27, 28, 29. The first, second and third ends 27, 28, 29 are spatially curved toward one another and embrace the foot in the area of a cap of the lower extremity and connected with one another by the above mentioned fixing elements 31. The fourth end 30 is formed free and located under the foot along its whole length. Two elastic braces 32 each connect correspondingly to the above mentioned first and second flexible belt 22,23, with the above mentioned cap-sole element 26 in the area of the cap with the possibility of regulation of a distance therebetween.

The means for interaction 20, 24 and fixing elements 25, 31 can be formed of any known construction for analogous purposes.

Figure 3:
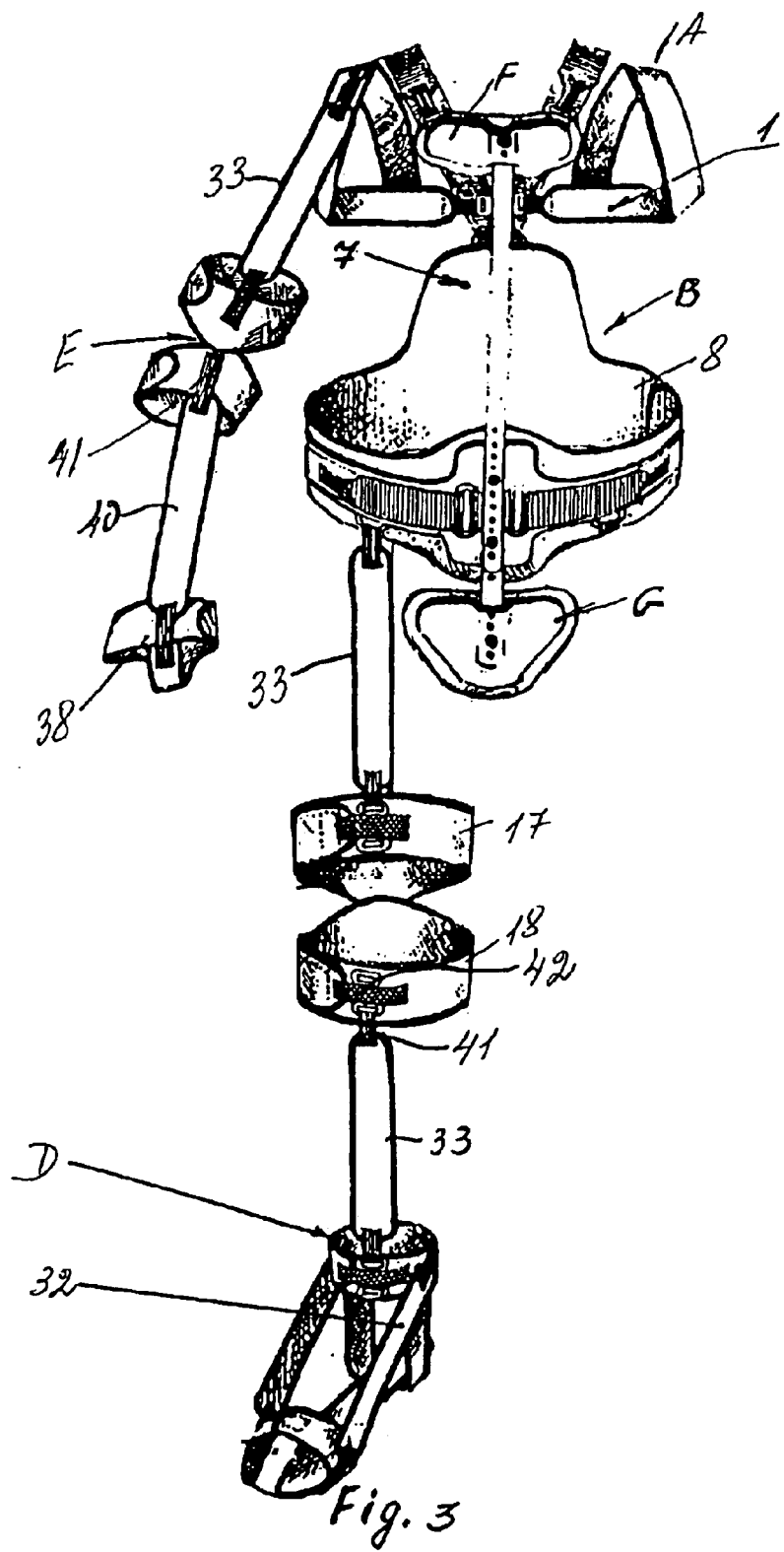
FIG. 3 is a view showing the proposed device in perspective, in accordance with the third embodiment.
Figure 4:
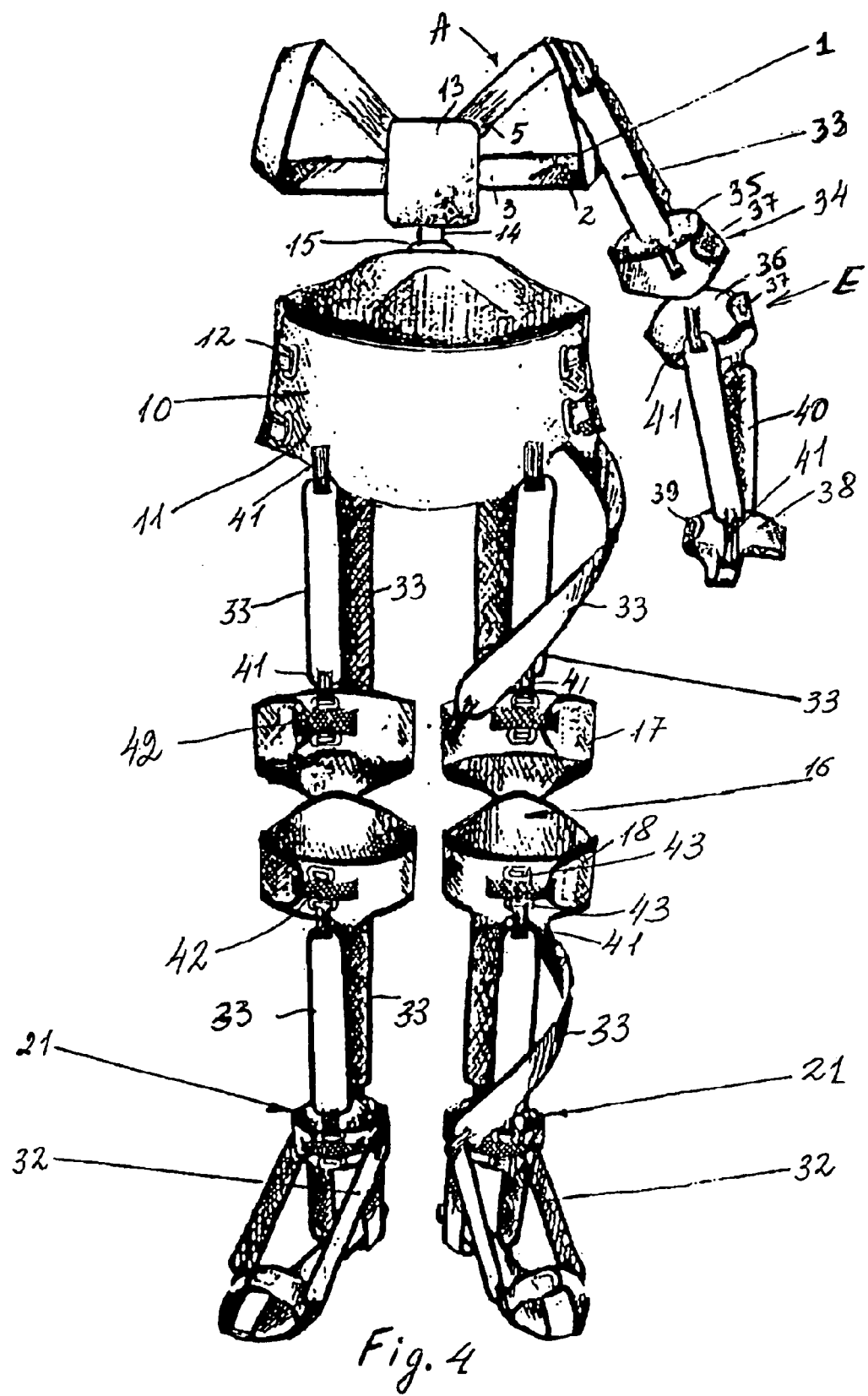
FIG. 4 is a view showing the proposed device in perspective, in accordance with the fourth embodiment.

In addition the proposed device contains many correcting-rotation elements 33 which consecutively connect the second, third and fourth modules with the possibility of their disconnection. The number of the correcting-rotation elements 33 depends on pathology of the user. For example in FIGS. 1 and 2 the devices are proposed, each having four correcting-rotation elements 33 provided for the connection of the second and third modules. FIG. 3 shows the proposed device with one correcting-rotation element 33 for connection of the second and third modules. FIG. 4 shows the proposed device with five correcting-rotation elements 33 for connection of the second and third modules.

In addition, in condition of corresponding pathology of the user, the proposed device can contain at least one means 34 for correction of the upper extremity of the user's body, shown in FIGS. 2, 3, 4, 6, which performs the function of a fifth E of the plurality of modules and formed with the possibility of fixing of a shoulder and fore shoulder of the above mentioned upper extremity in a predetermined position with a freedom of movement of the elbow joint of the above mentioned upper extremity. When the user has a pathology of both upper extremities, there must be two means 34.

The above mentioned means 34 for correction of the above mentioned upper extremity includes a first spatially curved flexible strip 35 which embraces the upper extremity above its elbow joint and have a first end, a second end and a longitudinal edge having a medium part; a second spatially curved flexible strap 36 which embraces the upper extremity under the above mentioned elbow joint and having a first end, a second end and a longitudinal edge located opposite to the longitudinal edge of the first flexible band and having a medium part connected with the medium part of the longitudinal edge of the first flexible band 35. It also has a location of connection between the medium parts of the opposite longitudinal edges of the above mentioned first and second flexible bands 35, 36 and located in an under-elbow area of the upper extremity, a first means of interaction 37 connecting the first end and the second end of the first flexible strip 35 for fixing of the first flexible strip 35 under the above mentioned elbow joint of the possibility of regulation of a distance between the above mentioned end; a second means for interaction 37 connecting the first end and the second end of the second flexible strap of the above mentioned bandage of shoulder and fore shoulder for fixing the second flexible strip 36 under the elbow joint and the possibility of regulation of the distance between the above mentioned ends; a hand flexible element 38 which is ergonomically suitable for fixing on the palm and deflecting of a thumb of the upper extremity and having a V-shaped, a first and a second end each provided with a means 39 for fixing on the palm of the upper extremity with the possibility of regulation of the tightening force of the hand flexible element 38, at least one elastic brace 40 formed analogously to the correcting-rotation elements 33 and connecting the hand flexible element 38 with the second flexible strip 36 of having a first end and a second end, a means 41 of connection provided on each of the first and second ends of the elastic brace 40 and regulating tensioning of the above mentioned elastic brace 22 in the place of its connection with the hand flexible element 28 and the second flexible strip 26.

The fifth module is connected with the possibility of its disconnection with the first module by correcting-rotation elements 33 formed analogously to the above. The number of the correcting-rotation element 33 depends on user's pathology. For example in FIG. 1 there is a device, in which there are two correcting-rotation elements 33 proposed for connection of each fifth and first modules, FIG. 3 shows the proposed device for one correcting-rotation element 33 for correction of the fifth and fourth module, and FIG. 4 shows the proposed device with two correcting rotation elements 33 for connection of the fifth and first modules.

The outer surface of each of the plurality of modules is composed of a material which has a nap suitable for the use of a Velcro-type connection. Each of the above mentioned plurality of correcting-rotation elements 33 and each elastic brace 40 is formed as a band of elastic material with a relative stretching of 5–50% and provides correction of movement of the user during its displacement and/or operation.

Each of the correcting-rotation elements 33 and each of the elastic braces 40 is formed of a material having a stretching providing a correction which corresponds to the user's pathology, for example from the fabric "tricor" and "neopren".

Each of the above mentioned correcting-rotating elements 33 has means 41 of connection which regulate a tensioning of the above mentioned correcting-rotation element 33 in each place of their connection with each of the plurality of modules. Each means of connection 41 has an engaging surface for providing a Velcro-type connection in any place of the outer surface of each of the plurality of models, depending on the user's pathology.

The above mentioned correcting-rotation element 33 can connect the above mentioned modules with the use of the means 44 directly as described herein above (FIG. 8). However this connection can be performed by placing-connecting means 42 each formed of two layers connected with one another. The outer surface of the first layer is composed of a material having a nap suitable for the use of a Velcro-type connection, the outer surface of the second layer is formed engaging suitable for the use of the Velcro-type connection. Each of the placing-connecting means 42 has at least one strap 43. Each of the plurality of means 41 for connection provided on each of the plurality of correcting-rotation elements 33 must have a nap surface for a Velcro-type connection. Each of the correcting-rotation element 33 can have a means 44 for changing of its length. The means 44 shown in FIG. 9 can be formed as a fixator composed of two oval elements. Alternatively, it can have another known construction for analogous purposes. As explained herein above, each of the modules A, B, C, D, E, of the proposed device, depending on the user's pathology, can be used autonomously, independently from other modules. For example, the first module A can be used as an autonomous device 45 in FIG. 7 for treatment of patients with impermanent of the function of muscles of the shoulder belt.

The third and fourth modules C, D, can be used an autonomous device 46 shown in FIG. 5 for treatment of patients with impermanent of the functions of the lower extremities. The fixed module E can be used as an autonomous device 47 shown in FIG. 6 for treatment of patients with an impermanent of the function of the upper extremities. The proposed device operates in the following manner. Let us consider an embodiment when the user's pathology requires the use of the proposed device as a whole or in other words the proposed device which connects first, second and third, fourth and fifth modules. First the first and a second modules A, B are placed on the user and then third, fourth and fifth modules C, D, and E. The second module B in this case is a base for placing of power chains for the lower extremities. Depending on the user's pathology and medical prescriptions connected with it, a number and the length of a correcting-rotation elements 13 are determined for connection of the corresponding modules. Then, the third and the fourth modules C, D are connected by the correction-rotating element 33 with the second module B while the fifth module E is connected with the first module A so as to line the dosed power lines on the lower and upper extremities. The number and the length of the correcting-rotation elements 33 which is used for connecting of the corresponding modules is determined depending on the size of the user and his pathology. With the use of the means 41 of the connection, all modules are connected in accordance with the selected scheme.

Depending on the medical prescriptions, simultaneously with it being proposed device, also other known orthopedic attachments can be used, for example a various head holders can be used such as for example soft head holders, analogous to a shanz collar composed of various materials such as staff, particular, pneumatic and other constructions. In addition, it is possible to use various fixing devices, for example with orthopedic sole, shoe and orthopedic device which are fixed on the proposed device by their fixing elements. When the dynamic tests of the user in the assembled device are conducted, and if necessary a correction of the power chains is performed. During the process of the user proposed device when it is necessary it is possible to provide a correction of the length of the correction-rotation elements and also their position in the fixation to the outer surface of the corresponding module can be changed.

EXAMPLE 1

A patient C. B 32 Years Old.

Diagnosis: Compression breaking Th 12-L2 of vertebra with impermanent of the bone marrow. Weak cut of the lower extremities. During examination of the patient a hypotrophy of muscles of lower extremities was found, reflexes are weak. In the lying position, aquino-varus position of the feet was observed. In a vertical position the feet are placed in a flat-valgus pattern. Knee joints are not closed with four-head muscles. The function of the hip muscles is considerably weakened. The function of pelvic organs is practically preserved. Pronounced phenomena of post traumatic osteokhondrosis. Previously treatment in accordance with the known methods were performed without pronounced effect.

The above mentioned pathology (the presence of post-traumatic syndrome) prevents the use of the device in accordance with the patent of Russian Federation no. 2054907, since this device performs an action on the whole support-movement system of the user which is not advisable in this case.

The patient performed the treatment course during one month with the use of the proposed device including first, second, third and fourth modules.

A session of each treatment was 60 minutes and included treatment of the device during 20 minutes, a complex of treating physical imposition of standing, sitting, lying during 30 minutes. 25 sessions of five-day cycles with performed with breaks for one day. As a result of the treatment, an increase of physical perseverance was observed, as well as a muscle force of the lower extremities, a reduction of evening tiredness and pains in the back, considerable improvement of moving and static functions.

EXAMPLE 2

Patient: A. B. 12 Years.

Diagnosis: Made in the age of one year. A child cerebral paralysis, spasmatic dipligy. Intellect is retained. Pronounced impairment of the stateliness of the type (round back) is noted with the top of kifoziring at the height of noticeable age H8 Th10. Before it, medication, physiotherepeutic, orthopedic treatments were performed in accordance with known methods. The treatment was given a temporary affect with the subsequently repeat in increasing degree. It was recommend to the patient to use the proposed device including first, second, third and fourth modules.

The section of each treatment was 40 minutes and includes walking in the device during 10 minutes, couplings of treating physical in position standing, sitting lying during 20 minutes.

20 sessions of five-day cycles were performed with an interruption of two days. As a result of the treatment an improvement of the movement of the static function of patient and increase of its physical perseverance was observed.

EXAMPLE 3

Patient I.B. 52 Years.

Diagnosis: Acute interment of the brain blood circulation, left side hemipares, expanded osteohydrosis of spine, herniated discs L3, L4, L5 of vertebrae. The patient was treated in accordance with known methods without a significant and critical improvement.

The proposed device in accordance with the patent of Russian Federation 2054907 was impossible because of the spread osteohydrosis with each complications of root sympathomatics.

The proposed device was recommended to the patient, and included first, second, third, fourth and fifth modules. The action of its treatment was 45 minutes and included a walking in the device during 15 minutes in complex of treatment physicals in position of standing, sitting, lying during 20 minutes.

The treatments were performed under the control of arterial blood pressure. 20 sessions of five-day cycles were performed with two days of rest in between.

As a result of the treatment a reduction of pathological tonus in a large chest muscle was observed, which made possible an increase of volume of movement of the upper extremities, an increase of tonus of delta-shaped muscle, elimination of subluctation features. In the waste area, a tendency toward reducing of antalgic scoliosis and subjective improvement of root symptomatic was observed.

It will be understood that each of the elements described above, or two or more together, may also find a useful application in other types of constructions differing from the types described above.

While the invention has been illustrated and described as embodied in device for user's suffering from sequels of central nervous system and locomotorium affection of body, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by letters Patent is set forth in the appended claims:

What is claimed is:

1. A device for users with sequels of central nervous system affections and/or locomotorium affection of a body, which includes a recliner located in an upper area of the above mentioned user's body and attachments for moving apart of on-shoulder parts and moving shoulder blades to the spine; means for correcting of medium area of the user's body located in the region of a waste, means for correcting a hip and a shin of a lower extremity formed with a possibility of fixing of the above mentioned hip and shin and a predetermined position, means for correcting of shin-foot joint and fingers of a lower extremity, formed with the possibility of fixing of a foot of the above mentioned lower extremity relative to the shin-foot joint, a plurality of correcting-rotating elements and a plurality of connecting elements, wherein in accordance with the present invention the above mentioned elements are formed as a plurality of modules which cover certain parts of the user's body and each of which is formed with the possibility of a separate use and which include a recliner performing the functions of a first of the above mentioned modules; means for correcting of the medium area of the above mentioned users body which performs the function of the second of the above mentioned plurality of modules and is suitable for correcting of the spine without a vertical load; at least one means for correcting of a hip and a shin of a lower extremity of the above mentioned user's body which performs the function of a third from the above mentioned plurality of modules and is formed with the possibility of fixing of the above mentioned hip and shin in a predetermined position with providing at the same time a freedom of movement of the knee joint of the above mentioned lower extremities; at least one means for correcting of a shin-foot joint and fingers of the lower extremity of the above mentioned user's body which performs the function of a fourth from the above mentioned plurality of modules which is formed with the possibility of fixing of the foot of the above mentioned lower extremity relative to the shin-foot joint in a frontal and sagital planes with providing a freedom of movement of the shin-foot joint; an exterior surface of each of the above mentioned plurality of modules is composed of a material which has a nap which is suitable for the use of a connection of the Velcro type; a plurality of correcting-rotating elements which successively connect of the above mentioned second, third and fourth modules so that they can be disconnected; each of the above mentioned plurality of correcting-rotating elements is formed as a band of elastic material with a relative stretching of 5–50% and provides a correctional movement of the user during its displacement; a plurality of connecting means provided on each of the above mentioned plurality of correcting-rotating elements which regulate the stretching of the above mentioned correcting rotating elements in each location of their connection with each of the above mentioned second, third, and fourth modules; each of the above mentioned plurality of means for connection have an engaging surface suitable for providing a connection of the Velcro type with the above mentioned outer surface of each of the above mentioned second, third, and fourth modules in any location of the surface depending on a pathology of the user.

2. A device as defined in claim 1, wherein each correcting-rotating element have a means for changing of its length.

3. A device as defined in claim 1, wherein said recliner includes a first flexible band and a second flexible band, each having a first end and a second end; each of the above mentioned first and second flexible bands is formed as spatially curved in form of a loop so that a first strap and a second strap are formed, each embracing a corresponding shoulder joint of the above mentioned user's body; means of interaction which connect the above mentioned first ends of the above mentioned first and the above mentioned flexible bands with the possibility of regulation of a distance between them and located on the back of the above mentioned user's body; the above mentioned second end of the above mentioned first flexible band is fixedly connected to the above mentioned first flexible band near the above mentioned first means of interaction; the above mentioned second end of the above mentioned second flexible band is fixedly connected to the above mentioned second flexible band near the above mentioned first means of interaction.

4. A device as defined in claim 1; and further comprising an elastic plate which covers a portion of the above mentioned user's back in the zone of shoulders, located between the recliner and the back of the user; the outer surface of the above mentioned plate is composed of a material which has nap suitable for the use of the Velcro-type connection and provided for connection of the above mentioned first and second straps of the above mentioned recliner; inner side of each of the above mentioned first and second straps have an engaging surface for providing a connection of the Velcro type with the above mentioned outer surface of the above mentioned plate; a connecting means arranged on the lower part of the above mentioned flexible plate and provided for connection with the above mentioned second module.

5. A device as defined in claim 1, wherein said means for correction of the medium part of the above mentioned user's body contains a corset which has a complicated profiled shape providing a correction of the above mentioned spine without the vertical load, a first part of the above mentioned corset embraces the above mentioned user's body in the area of the above mentioned waste and has means for fixing of this part on the above mentioned user's body in a transverse direction; a second part of the above mentioned corset which covers the above mentioned back in the zone of shoulder blades.

6. A device as defined in claim 4, wherein said means of correction of the medium area of the above mentioned user's body includes corset which has a complicated profiled shape which provides correction of the above mentioned spine without a vertical load and embraces the above mentioned user's body in the area of the above mentioned waste and has means for its fixation on the above mentioned user's body in a transverse direction; connecting means form with the possibility of connection with the above mentioned connecting means of the above mentioned flexible spring.

7. A device as defined in claim 1, wherein said means for connecting a hip and shin of the above mentioned lower extremity connect a first flexible bandage which embraces the above mentioned lower extremity above its knee joint and has a first end, a second end and a transverse edge which has a medium part; a second flexible bandage which embraces the above mentioned lower surface under the above mentioned knee joint and has a first end, a second end and a transverse edge located opposite to the above mentioned longitudinal edge of the above mentioned first flexible bandage and has a medium part, connected with the above mentioned medium part of the above mentioned longitudinal edge of the above mentioned first flexible bandage; a location of connection of the above mentioned medium part of the above mentioned opposite longitudinal edges of the above mentioned first and second flexible bandages is located in the area under the knee of the above mentioned lower extremity, first means of interaction which connects the above mentioned first end and the above mentioned second end of the above mentioned first flexible bandage for its fixation above the above mentioned knee joint with the possibility of regulation of a distance between the above mentioned ends; a second means of interaction which connects the above mentioned first end and the above mentioned second end of the above mentioned second flexible bandage for its fixation under the above mentioned knee joint with the possibility of regulation of distance between the above mentioned ends.

8. A device as defined in claim 1, wherein said means for correction of the shin-foot joint and fingers of the above mentioned lower extremity contain a first flexible belt which embraces the ankle of the above mentioned lower extremity and has a first end and a second end; and means of interaction for fixing of the above mentioned first flexible belt on the above mentioned ankle which connects the above mentioned first end and the second end of the above mentioned first flexible belt with the possibility of regulating a distance between these ends; a second flexible belt which embraces the above mentioned foot of the above mentioned lower extremity in the zone of its longitudinal arch and has a first end, a second end and a lower surface facing toward the above mentioned foot; the above mentioned first and second ends of the above mentioned second flexible belt connected to the above mentioned first flexible belt from the opposite lateral sides of the above mentioned ankle; a cap-sole element of a cross-shape which has a first, second, third and fourth ends on each of the above mentioned first, second and third ends there are fixing elements; the above mentioned first, second and third ends are spatially bent toward one another and embrace the above mentioned foot in the area of a cap of the above mentioned lower extremity and connected by the above mentioned fixing elements; the above mentioned fourth end is formed free and located under the above mentioned foot along its whole length; two elastic braces each connecting correspondingly the above mentioned first and the above mentioned second flexible belts with the above mentioned cap-sole element and the above mentioned area of the cap with the possibility of regulating of a distance between them.

9. A device as defined in claim 1; and further comprising a plurality of placing-connecting means for connection of the above mentioned plurality of the correcting-rotation elements with the corresponding one of the above mentioned plurality of modules; each of the above mentioned plurality of the placing-connecting means includes two layers; an outer surface of first of the layers is formed from a material which has a nap suitable for a Velcro-type connection; an outer surface of the second layer is formed as engaging and suitable for the use of the Velcro-type connection; at least one strap fixedly connected on each of the above mentioned plurality of the placing-connecting means; each of the above mentioned plurality of the connecting means on each of the above mentioned correcting-rotating elements has a nap surface suitable for a Velcro-type connection.

10. A device as defined in claim 1; and further comprising at least one means for correction of an upper extremity of the above mentioned user-s body which performs the function of a fifth of the above mentioned plurality of modules, formed with the possibility of fixing of shoulder and fore shoulder of the above mentioned upper extremity in the predetermined position with providing of a freedom of movement of the elbow joint of the above mentioned upper extremity; an outer surface of the above mentioned fifth module is formed from the material which has a nap suitable for the use of a Velcro-type connection; at least one correcting-rotating element of the above mentioned means of correction of the upper extremity each connects the above mentioned fifth modules with the above mentioned first module with the possibility of their disconnection; the above mentioned correcting-rotating element of the above mentioned means for correction of the upper extremity is formed as a band from an elastic material with relative stretching of 5–50% and provides a correctional movement of the above mentioned upper extremity during its operation; and means of connection provided on the above mentioned correcting-rotating element of the above mentioned means for correction of the upper extremity, which regulates the tightening of the above mentioned correcting-rotating element at a location of its connection with each of the above mentioned first and fifth modules and has an engaging surface suitable for providing a Velcro-type connection at any location of the above mentioned outer surfaces of the above mentioned first and second modules depending on the pathology of the user.

11. A device as defined in claim 10, wherein each of the above mentioned correcting-rotating elements of the above mentioned means for correction of the upper extremity has a means for changing of its length.

12. A device as defined in claim 10, wherein said means for correction of the above mentioned upper extremity has a first spatially curved flexible strip which embraces the above mentioned upper extremity under its above mentioned elbow joint and has a first end, a second end and a longitudinal edge having a medium part; a second spatially curved flexible strip which embraces the above mentioned upper extremity under the above mentioned elbow joint and has a first end, a second end and a longitudinal edge located opposite to the above mentioned longitudinal edge of the above mentioned first strip and having a medium part fixedly connected with the above mentioned medium part of the above mentioned longitudinal edge of the above mentioned first flexible strip; a location of the fixed connection of the above mentioned medium part of the above mentioned opposite longitudinal edges of the above mentioned first and second flexible strips is located in an under-elbow area of the above mentioned upper extremity; a first means of interaction which connects the above mentioned first end and the above mentioned second end of the above mentioned first flexible strip for fixation of the above mentioned first flexible strip above the above mentioned elbow joint with the possibility of a regulation of the distance between the above mentioned ends; a second means of interaction which connects the above mentioned first end and the above mentioned second end of the above mentioned second flexible strip of the above mentioned bandage of a shoulder and the fore shoulder for fixation of the above mentioned second flexible strip above the above mentioned elbow joint with the possibility of regulation of a distance between the above mentioned ends; a hand flexible element which is ergonomically suitable for fixing on a pump and deflecting of a thumb of the above mentioned upper extremity and having a V-shaped, a first end and a second end, each of which has a means for fixation on the hand of the above mentioned upper extremity with the possibility of regulation of a tightening of force of the above mentioned hand flexible element; at least one elastic brace which connects the above mentioned hand flexible element with the above mentioned second flexible strip and has a first end and a second end; and means for connecting having provided on each of the above mentioned first and second ends of the above mentioned elastic brace which regulates a tightening of the above mentioned elastic brace in the location of its connection of the above mentioned hand flexible element and the above mentioned second flexible band.

13. A device for users with sequels of central nervous system affections and/or locommotorium affection of a body, comprising a plurality of modules which cover certain areas of the user's body and each form with a possibility of a separate use; a recliner which performs the function of the first of the above mentioned plurality of modules and located in the upper area of the user's body and suitable for spreading of above shoulder areas and moving of the shoulder blades toward the spine; the above mentioned recliner contains a first flexible band and a second flexible band each having a first end and a second end; each of the above mentioned first and second flexible bands is formed as a spatially curved band in form of a loop so that a first strap and a second strap are formed, each embracing a corresponding shoulder joint of the above mentioned user's body; and means for interaction which connects the above mentioned first and the above mentioned second flexible bands with the possibility of regulation of a distance between them and located on a back of the user's body; the above mentioned second end of the above mentioned first flexible band is fixedly connected to the above mentioned first flexible band near the above mentioned first means of interaction; the above mentioned first end of the above mentioned second flexible band which is fixedly connected to the above mentioned second flexible band near the above mentioned first means of interaction; and means for correction of a medium area of the above mentioned user's body which performs the function of the second of the above mentioned plurality of modules and located in the area of waste and suitable for correction of the above mentioned spine without a vertical load; and means for correcting of a medium area of the above mentioned user's body which includes a corset having a complicated profiled shape which provides a correction of the above mentioned spine without a vertical load; a first part of the above mentioned corset embraces the above mentioned user's body in the area of waste and have a means for fixing of this part of the above mentioned user's body in a transverse direction; a second part of the above mentioned corset covering a back of the above mentioned user's body in the zone of shoulders; at least one means for correction of a hip and shin of lower extremity of the above mentioned user's body which performs the function of a third of the above mentioned plurality of modules and formed with the possibility of fixing of the above mentioned hip and shin in the predetermined position with providing a freedom of movement of a knee joint of the above mentioned lower extremity; the above mentioned means for correction of the hip and shin of the above mentioned lower extremity of the above mentioned user's body contains a first flexible bandage which embraces the above mentioned lower extremity above its above mentioned knee joint and having a first end, a second end and a longitudinal edge having a medium part; a second flexible bandage which embraces the above mentioned lower extremity under the above mentioned knee joint and has a first end, a second end and a longitudinal edge located above the above mentioned longitudinal edge of the above mentioned first bandage and having a medium part fixedly connected with the above mentioned medium part of the above mentioned longitudinal edge of the above mentioned first flexible bandage; a location of the fixed connection of the above mentioned medium parts of the above mentioned opposite longitudinal edges of the above mentioned first and second flexible bandage is located in an area under the knee of the above mentioned lower extremities; a first means of interaction which connects the above mentioned first end and the above mentioned second end of the above mentioned first flexible bandage for its fixation above the above mentioned knee joint with the possibility of regulation of the distance between the above mentioned ends; a second means of interaction connecting the above mentioned first end and the above mentioned second end of the above mentioned second flexible bandage for its fixation above the above mentioned knee joint with the possibility of regulation of a distance between the above mentioned ends; at least one means for correction of a shin-foot joint and fingers of the lower extremity of the above mentioned users body which forms the function of a fourth from the above mentioned plurality of modules and formed with the possibility of fixing of the foot of the above mentioned lower extremity relative to the shin-foot joint in a frontal and sagittal planes with providing a freedom of movement of the shin-foot joint of the above mentioned lower extremities; the above mentioned means for correction of the shin-joint foot and fingers of the above mentioned lower extremity includes a first flexible belt which embraces an angle of the above mentioned lower extremity and has a first end and a second end; and means for interaction for fixing of the above mentioned first flexible belt on the above mentioned ankle and connecting the above mentioned first end and second end of the above mentioned first flexible belt with the possibility of regulation of a distance between these ends; a second flexible belt which embraces the above mentioned foot of the above mentioned lower extremity in the zone of its longitudinal arch and has a first end and a second end; the above mentioned first and second ends of the above mentioned second flexible belt are fixed to the above mentioned first flexible belt from the opposite lateral sides of the above mentioned angle; a cap-under sole element having a cross-shape and having a first, second, third and fourth ends, with fixed elements provided on the above mentioned first, second and third ends; the above mentioned first, second and third ends are spatially curved toward one another and embrace the above mentioned foot in the area of the cap of the above mentioned lower extremity and connected by the above mentioned fixing elements; the above mentioned fourth end is formed free and located under the above mentioned foot along all its length; two elastic braces each connecting correspondingly the above mentioned first and the above mentioned second flexible belts with the above mentioned cap-undersole element in the above mentioned area of the cap with the possibility of regulation of a distance between them; the outer surface of each of the above mentioned plurality of modules is formed of a material having a nap which is suitable for the use of a Velcro-type connection; a plurality of correcting-rotation elements which consecutively connect of the above mentioned second, third, and fourth modules with the possibility of their disconnection; each of the above mentioned plurality of correcting-rotating elements is formed as a band of an elastic material with a relative stretching 5–50% and providing a correction of the user's movement during its displacement; a plurality of means for connection on each of the above mentioned plurality of the correcting-rotating element which regulate a tightening of the above mentioned correcting-rotating elements in each place of their connections with each of the above mentioned second, third and fourth modules; each of the above mentioned plurality of the means for connection have an engaging surface suitable for providing a Velcro-type connection with the above mentioned outer surface of each of the above mentioned second, third and fourth modules in any place of this surface, depending on the pathology of a user.

14. A device as defined in claim 13, wherein each of the correcting-rotating elements has a means for changing of its length.

15. A device as defined in claim 13; and further comprising at least one means for correcting of the upper extremity of the above mentioned user's body which performs the function of a fifth of the above mentioned plurality of modules and is formed with a possibility of fixing of a shoulder and fore-shoulder of the above mentioned upper extremity in the predetermined position with providing a freedom of movement of an elbow joint of the above mentioned upper extremity, wherein the above mentioned means for correction of the above mentioned upper extremity includes a first spatially curved flexible band which embraces the above mentioned upper extremity above its above mentioned elbow joint and having a first end, a second end a longitudinal edge having a medium part, a second spatially curved flexible band which embraces the above mentioned upper extremity under the above mentioned elbow joint and has a first end, a second end and a longitudinal edge located opposite to the above mentioned longitudinal edge of the above mentioned first flexible strip and having a medium connected with the above mentioned medium part of the above mentioned longitudinal edge of the above mentioned first flexible strip; a place of connection of the above mentioned medium parts of the above mentioned medium parts of the above mentioned opposite longitudinal edges of the above mentioned first and second flexible strips is located in an under-elbow area of the above mentioned upper extremities; a first means of interaction which connects the above mentioned first end and the above mentioned second end of the above mentioned first flexible strip for fixing of the above mentioned first flexible strip above the above mentioned elbow joint with the possibility of regulation of a distance between the above mentioned ends; and second means for interaction which connects the above mentioned first end and the above mentioned second end of the above mentioned first flexible strip of the above mentioned bandage of shoulder and fore shoulder for fixing of the above mentioned second flexible strip under the above mentioned elbow joint with the possibility of regulation of a distance between the above mentioned ends; a hand flexible element which is ergonomically suitable for fixing on a pump and moving of a thumb of the above mentioned upper extremity and having a V-shape, a first end and a second end each of which has a means for fixation on the palm of the above mentioned upper extremity with the possibility of regulation of the tightening force of the above mentioned hand flexible element; at least one elastic brace which connects the above mentioned hand flexible element with the above mentioned second flexible strip and has a first end and a second end; and means for connecting provided on each of the above mentioned first and second above mentioned elastic brace and regulating a tightening of the above mentioned elastic brace in the place of its connection with the above mentioned hand flexible element and the above mentioned second flexible strip; analogous surface of the above mentioned fifth module formed from the material having a nap suitable for a Velcro-type connection; at least one correcting-rotation element of the above mentioned means for correction of the upper extremity which connects the above mentioned fifth module with the above mentioned first module with the possibility of their disconnection, the above mentioned correcting-rotating element of the above mentioned means for correcting of the upper extremity is formed as a band from an elastic material with a relative stretching of 5–50% and provides a correction of movement of the above mentioned upper extremity during its operation; and means for connection provided on the above mentioned correcting-rotation element of the above mentioned means for correction of the upper extremity and regulating a tightening of the above mentioned correction-rotation element in the place of its connection with each of the above mentioned first and fifth modules and having an engaging surface suitable for providing a Velcro-type connection in any place of the above mentioned outer surfaces of the above mentioned fifth and first modules depending on the pathology of the user.

16. A device as defined in claim 15, wherein each of the above mentioned correcting-rotation elements of the above mentioned means for correction of the upper extremity has a means for changing of its length.

17. A device for users with sequels of central nervous system and/or locomotorium affection of a body, comprises a plurality of modules covering certain areas of the user's body each of which is formed with the possibility of a separate use; a recliner performing the function of a first of the above mentioned modules and located in the upper area of the above mentioned user's body and suitable for moving a part of above-shoulder area and moving the shoulder blades toward the spine, wherein the above mentioned recliner includes a first flexible band and a second flexible band each having a first end and a second end; each of the above mentioned first and second flexible bands is formed spatially curved as a loop such that a first strap and a second strap are formed, each embracing a corresponding shoulder joint of the above mentioned user's body; and means for interaction connecting the above mentioned first ends of the above mentioned first and the above mentioned second flexible bands with the possibility of regulation of a distance between them as located on a back of the above mentioned user's body; the above mentioned second end of the above mentioned first flexible band is fixedly connected on the above mentioned first flexible band near the above mentioned first means of interaction; the above mentioned second end of the above mentioned second flexible band is fixedly connected on the above mentioned second flexible band near the above mentioned first means of interaction; and means for correction of a medium area of the above mentioned user's body which performs the function of a second of the above mentioned modules and is located in the area of a waste and suitable for correction of the above mentioned spine without a vertical load; and the above mentioned means for correction of the medium area of the above mentioned user's body includes a corset having a complicated profiled shape which provides a correction of the above mentioned spine without the vertical load; a first part of the above mentioned corset embraces the above mentioned user's body in the area of the above mentioned waste and has a means for fixing of this part on the above mentioned user's body in a transverse direction; a second part of the above mentioned corset covers a back of the above mentioned user's body in the zone of shoulder blades; at least one means for correction of a hip and shin of the lower extremity of the above mentioned user's body performs the function of the third of the above mentioned plurality of modules and is formed with a possibility of fixing of the above mentioned hip and shin in a predetermined position is providing a freedom of movement of the above mentioned knee joint of the above mentioned lower extremity, wherein the above mentioned means for correction of hip and shin of the above mentioned lower extremity includes a first flexible bandage which embraces the above mentioned lower extremity above the above mentioned knee joint and has a first end, a second end and a longitudinal edge having a medium part; a flexible bandage which embraces the above mentioned lower extremity under the above mentioned knee joint and has a first end, a second end and a longitudinal edge located opposite to the above mentioned longitudinal edge of the above mentioned first flexible bandage and has a medium part fixedly connected with the above mentioned medium part of the above mentioned longitudinal edge of the above mentioned first flexible bandage; a place of fixed connection of the above mentioned medium parts of the above mentioned opposite longitudinal edges of the above mentioned first and second flexible bandages is located in an under-knee area of the above mentioned lower extremity; the first means of interaction connects the above mentioned first ends and the above mentioned second end of the above mentioned first flexible bandage for its fixation above the above mentioned knee joint with the possibility of regulation of a distance between the above mentioned ends; second means for interaction which connects the above mentioned first end and the above mentioned second end of the above mentioned second flexible bandage for its fixation under the above mentioned knee joint with the possibility of regulation of distance between the above mentioned ends; at least one means of correction of the shin-foot joint and fingers of the lower extremity of the above mentioned user's body which performs the function of fourth of the above mentioned plurality of modules and is formed with the possibility of fixation of the foot of the above mentioned lower extremity relative to the shin-foot joint in a frontal and sagittal surfaces with the possibility of a movement of freedom of the shin-foot joint, and the above mentioned means of correction of the shin-foot joint and fingers of the above mentioned lower extremities includes a first flexible belt which embraces an ankle of the above mentioned lower extremity and has a first end and a second end; and means for interaction for fixing of the above mentioned first flexible belt on the above mentioned ankle and connects the above mentioned first and the above mentioned second end of the above mentioned first flexible belt with the possibility of regulation of a distance between these ends; a second flexible belt which embraces the above mentioned foot of the above mentioned lower extremity in the zone of its longitudinal arch and has a first end and a second end; the above mentioned first and second ends of the above mentioned second flexible belt are fixed to the above mentioned first flexible belt from the opposite lateral sides of the above mentioned ankle; a cap-sole element having a cross shape and a having a first, second, third and fourth ends with fixing elements on each of the above mentioned first, second and third ends; the above mentioned first, second and third ends are spatially curved toward one another and embrace the above mentioned foot in the area of the cap of the above mentioned lower extremity and are connected by the above mentioned fixing elements; the above mentioned fourth end is formed free and located under the above mentioned foot along its whole length, two elastic braces each connecting correspondingly the above mentioned first and the above mentioned flexible belts with the above mentioned cap-sole element in the above mentioned area of the cap with the possibility of regulation of distance between them; at least one means of correction of the upper extremity of the above mentioned user's body which performs the function of the fifth of the above mentioned plurality of modules and formed with the possibility of fixing of a shoulder and fore shoulder of the above mentioned upper extremity in a predetermined position with providing a freedom of movement of the elbow joint of the above mentioned upper extremity, with the above mentioned means for correction of the above mentioned upper extremity containing a first spatially curved flexible strip which embraces the above mentioned upper extremity above the above mentioned elbow joint and having a first end, a second end and a longitudinal edge having a medium part; a second spatially curved flexible scrip which embraces the above mentioned upper extremity under the above mentioned elbow joint and having a first end, a second end and a longitudinal edge located opposite to the above mentioned longitudinal edge of the above mentioned first flexible strip and having a medium part connected with the above mentioned medium part of the above mentioned longitudinal edge of the above mentioned flexible strip; a place of connection of the above mentioned medium parts of the above mentioned opposite longitudinal edges of the above mentioned first and second flexible strips is located in an under elbow area of the above mentioned upper extremity; a first means of interaction connecting the above mentioned first end and the above mentioned second end of the above mentioned first flexible strip for fixation of the above mentioned first flexible strip above the above mentioned elbow joint with the possibility of regulation of a distance between the above mentioned ends; a second means of interaction connecting the above mentioned first end and the above mentioned second end of the above mentioned second flexible strip of the above mentioned band-shoulder and fore shoulder for fixing an above mentioned second flexible strip under the above mentioned elbow joint with the possibility of regulation of a distance between the above mentioned ends; a hand flexible element ergonomically suitable for fixing on the palm and moving of a thumb of the above mentioned upper extremity and having a V-shape, a first end and a second end each having a means for fixation on the palm of the above mentioned upper extremity with a possibility of regulation of a tensioning force of the above mentioned canned flexible element; at least one elastic brace connecting the above mentioned hand flexible element with the above mentioned second flexible strip and having a first end and a second end; means for connecting provided on each of the above mentioned first and second ends of the above mentioned elastic brace and regulating a tensioning of the above mentioned elastic brace in the place of its connection with the above mentioned hand flexible element and the above mentioned second flexible strip; an outer surface of each of the above mentioned plurality of modules is formed from a material having a nap suitable for the use of a Velcro-type connection; a plurality of correcting-rotating elements consecutively connecting the above mentioned second, third and fourth modules with the possibility of their disconnection and the above mentioned fifth module with the above mentioned first module with the possibility of their disconnection; each of the above mentioned plurality of correcting-rotation elements is formed as a band of an elastic material with a relative stretching of 5–50% and providing a correction movement of the user during its displacement and/or operation; a plurality of means for connection provided on each of the above mentioned plurality of the correcting-rotation element and regulating a tightening of the above mentioned correction-rotating element in each place of their connection with each of the above mentioned plurality of modules; each of the above mentioned plurality of means for connection having an engaging surface suitable for providing a Velcro-type connection in any place of the above mentioned outer surfaces of which of the above mentioned plurality of modules depending on the users pathology.

18. A device as defined in claim 17, wherein each of the above mentioned correcting-rotation elements has a means for changing of its length.

* * * * *